(12) United States Patent
Benhamou et al.

(10) Patent No.: US 10,300,133 B2
(45) Date of Patent: May 28, 2019

(54) COMPOSITIONS FOR DELIVERY OF FOOD ALLERGENS TO THE STOMACH

(71) Applicant: DBV TECHNOLOGIES, Montrouge (FR)

(72) Inventors: Pierre-Henri Benhamou, Paris (FR); Christophe Dupont, Clamart (FR); Stefan (Johan) Koppelman, Eg de Bilt (NL); Laurent Martin, Rueil Malmaison (FR); Hervé Brochard, Gerstheim (FR); Estelle Foucher, Kienheim (FR)

(73) Assignee: DBV TECHNOLOGIES, Montrouge (FR)

( * ) Notice: Subject to any disclaimer, the term of this patent is extended or adjusted under 35 U.S.C. 154(b) by 0 days.

(21) Appl. No.: 15/423,820

(22) Filed: Feb. 3, 2017

(65) Prior Publication Data
US 2017/0151325 A1   Jun. 1, 2017

Related U.S. Application Data

(63) Continuation-in-part of application No. PCT/EP2015/067853, filed on Aug. 3, 2015.

(30) Foreign Application Priority Data

Aug. 4, 2014  (EP) ..................... 14179711

(51) Int. Cl.
*A61K 39/35* (2006.01)
*A61K 9/50* (2006.01)
(Continued)

(52) U.S. Cl.
CPC ............. *A61K 39/35* (2013.01); *A61K 9/50* (2013.01); *G01N 33/6854* (2013.01); *A61K 2039/542* (2013.01); *G01N 2800/52* (2013.01)

(58) Field of Classification Search
CPC .... A61K 2039/542; A61K 39/35; A61K 9/50; G01N 2800/52; G01N 33/6854
See application file for complete search history.

(56) References Cited

U.S. PATENT DOCUMENTS

| | | | | | |
|---|---|---|---|---|---|
| 3,829,589 | A | * | 8/1974 | Matsunaga | A23L 25/30 426/427 |
| 4,786,508 | A | * | 11/1988 | Ghebre-Sellassie | A61K 9/5026 424/482 |
| 2005/0063994 | A1 | | 3/2005 | Caplan et al. | |

FOREIGN PATENT DOCUMENTS

| | | |
|---|---|---|
| EP | 0 608 950 | 8/1994 |
| EP | 2 245 946 | 4/2010 |

(Continued)

OTHER PUBLICATIONS

Grimshaw et al, "Presentation of allergen in different food preparations affects the nature of the allergic reaction—a case series," Clinical and Experimental Allergy, 33: 1581-1585, 2003.*
(Continued)

*Primary Examiner* — Kevin S Orwig
(74) *Attorney, Agent, or Firm* — Saliwanchik, Lloyd & Eisenschenk

(57) ABSTRACT

The invention relates to novel compositions and methods for diagnosing or treating food allergies. The invention particularly discloses new approaches for delivering food allergens to allergic patients by oral administration of formulations which dissolve and release proteins in the stomach. The invention allows the treatment of food allergies by delivering food allergens to the gut immune system with controlled exposure of the esophagus or oral cavity. The invention also allows to perform food challenges to assess the threshold of clinical reactivity without exposing the esophagus and oral (Continued)

Figure 1:
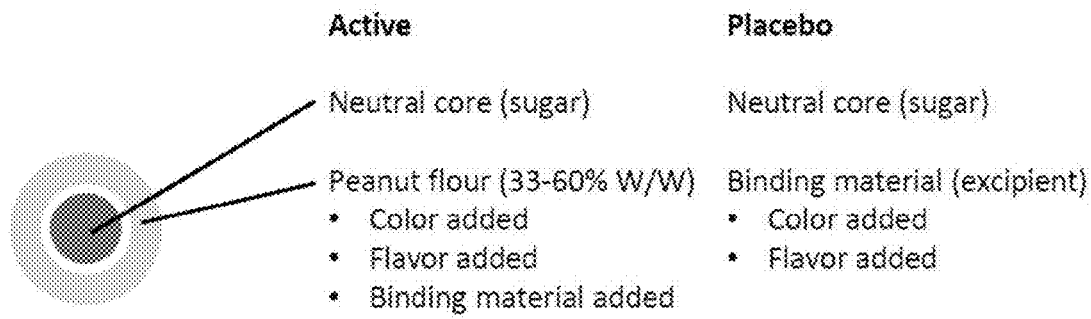

cavity. The invention may be used in any subject, particularly human subjects, and is applicable to any food allergen.

18 Claims, 12 Drawing Sheets
(3 of 12 Drawing Sheet(s) Filed in Color)

(51) Int. Cl.
*G01N 33/68* (2006.01)
*A61K 39/00* (2006.01)

(56) References Cited

FOREIGN PATENT DOCUMENTS

| WO | WO 2007/112747 | | 10/2007 | | |
|----|----------------|---|---------|---|---|
| WO | WO 2007/112750 | * | 10/2007 | ............. | A61K 39/36 |
| WO | WO 2011/018504 | | 2/2011 | | |
| WO | WO 2013/173697 | * | 11/2013 | ............. | A61K 39/35 |

OTHER PUBLICATIONS

Nowak-Wegrzyn, A. et al. "Work Group Report: Oral food challenge testing" *Journal of Allergy Clinical Immunology*, Jun. 1, 2009, pp. S365-S383, vol. 123, No. 6.
Written Opinion in International Application No. PCT/EP2015/067853, dated Oct. 1, 2015, pp. 1-5.
Nikam, V. K. et al. "Eudragit a Versatile Polymer : a Review" *Pharmacologyonline*, 2011, pp. 152-164, vol. 1.

* cited by examiner

Fig 3

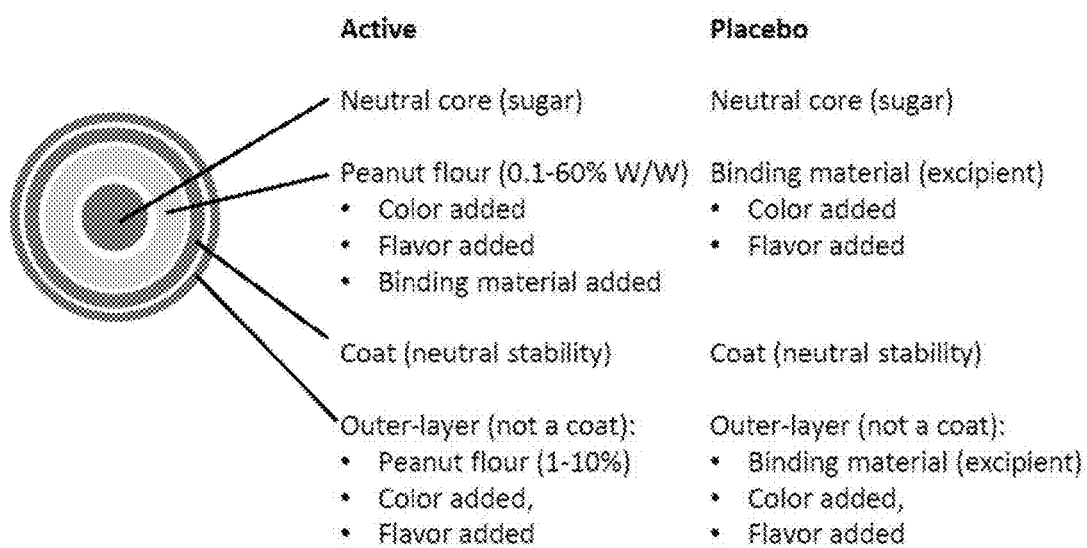

Active
- Neutral core (sugar)
- Peanut flour (0.1-60% W/W)
  * Color added
  * Flavor added
  * Binding material added
- Coat (neutral stability)
- Outer-layer (not a coat):
  * Peanut flour (1-10%)
  * Color added,
  * Flavor added Placebo
- Neutral core (sugar)
- Binding material (excipient)
  * Color added
  * Flavor added
- Coat (neutral stability)
- Outer-layer (not a coat):
  * Binding material (excipient)
  * Color added,
  * Flavor added

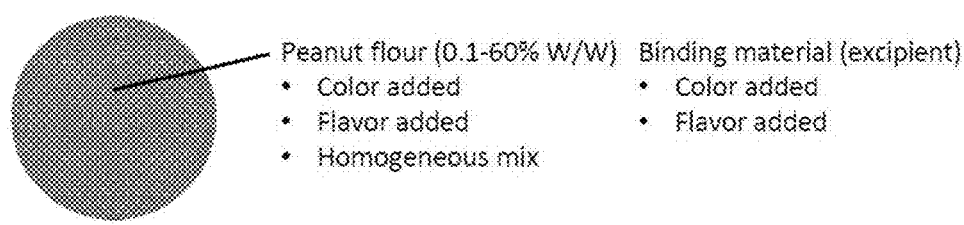

Active
- Peanut flour (0.1-60% W/W)
  * Color added
  * Flavor added
  * Homogeneous mix Placebo
- Binding material (excipient)
  * Color added
  * Flavor added

Fig 4

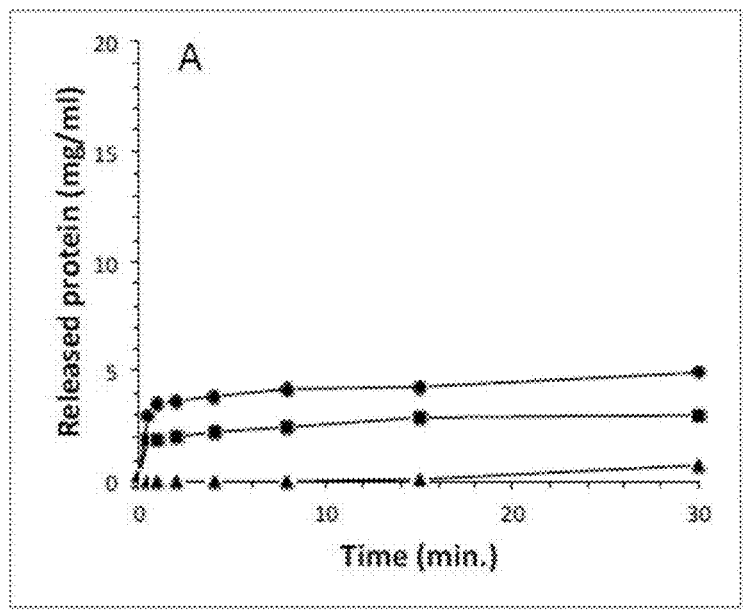
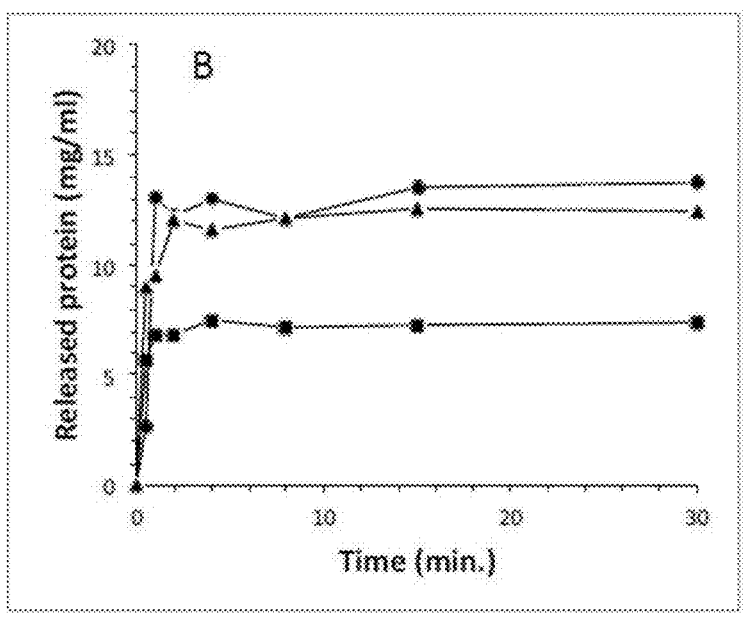
Fig 11

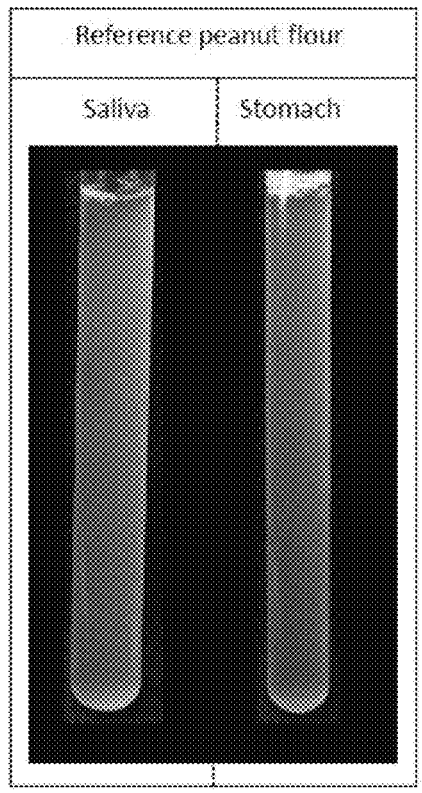
Fig 14 – Panel A
Fig 14 – Panel B
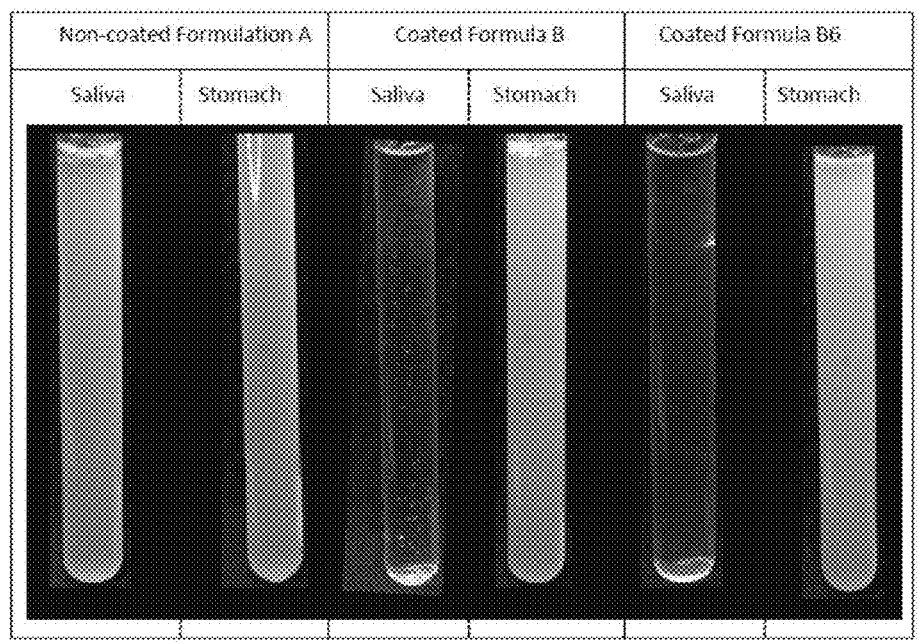

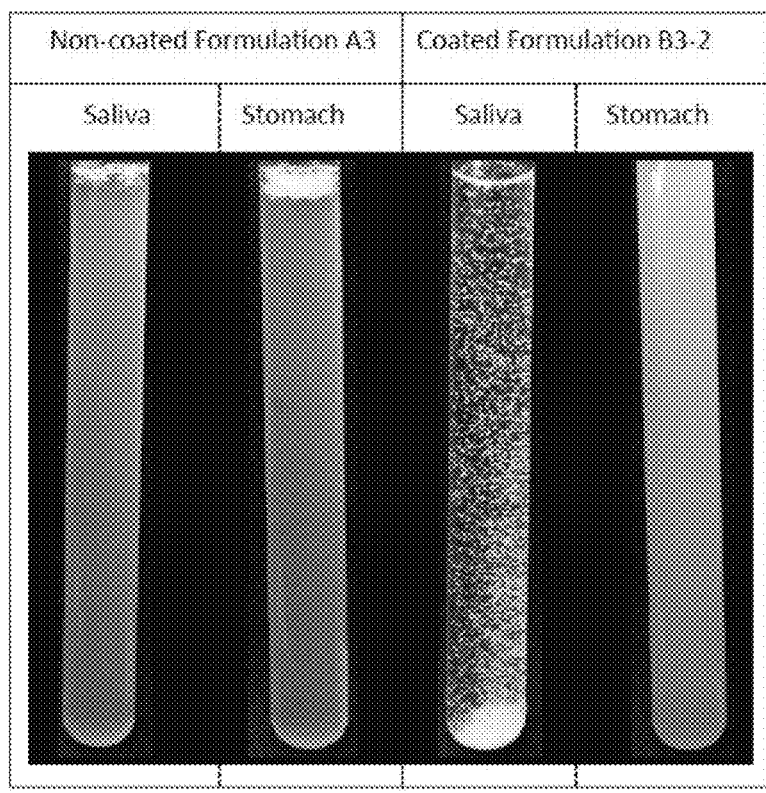
Fig 14 – Panel C

COMPOSITIONS FOR DELIVERY OF FOOD ALLERGENS TO THE STOMACH

CROSS-REFERENCE TO RELATED APPLICATION

This application is a continuation-in-part of PCT/EP2015/067853, filed Aug. 3, 2015, the disclosure of which is hereby incorporated by reference in its entirety, including all figures, tables and amino acid or nucleic acid sequences.

The invention relates to novel formulations of food allergens and the uses thereof. The invention particularly discloses new food allergen compositions, which dissolve in the upper digestive tract and allow controlled allergen exposure of the esophagus or oral cavity. The formulations of the invention are suitable for oral administration and may be used for oral immunotherapy of food allergies, for allergy detection and for food challenges, to assess the threshold of clinical reactivity with controlled exposure of the esophagus and oral cavity. The invention may be used in any subject, particularly human subjects, and is applicable to any food allergen.

INTRODUCTION

Food allergies affect up to 2% of the Western population with a main role for peanut, milk, egg, fish and crustaceans, and tree nuts and seeds as offending foods. The diagnosis of food allergy is based on an anamnesis, in vitro tests (presence of allergen-specific IgE in blood), skin reactivity tests with specific foods, in vivo provocation tests, or a combination of these approaches. The in vivo provocation test can be done in a double blinded, placebo-controlled fashion (DBPCFC) and this is considered the gold standard for food allergy diagnosis (Sampson, 2012).

One of the limitations of the DBPCFC is that there are no standardized materials for the food challenge. The difficult step is to mask the flavor of the food in question because patients may report subjective symptoms based only on the flavor (false-positive test result). Various recipes for food challenge material can be found in the literature, and some attempts to standardize were made (Cochrane et al, 2012). However, no products are on the market at this stage. Nowak recently published an international work group report on oral food challenge testing and elaborated on the use of various vehicles to mask the food. The original challenge vehicle chosen for blinding was opaque capsules (May CD, 1976). These are very effective at hiding nearly any food, especially additives and spices, but have significant limitations: (1) it is difficult to administer adequate quantities of food; (2) using processed food, such as dehydrated food, may destroy relevant allergens; (3) patients may have difficulty swallowing large or multiple capsules; and (4) capsules may be more resistant to digestion, result in delayed absorption (especially if part of the allergic reaction normally takes place in the mouth), and require longer dosing intervals of 30 to 60 minutes and longer observation periods of more than 2 hours. These limiting factors make such formulations not suitable for DBPCFC. Furthermore, they contain large amounts of allergens and their breaking up leads to step-by-step release of high levels of allergens, which may be dangerous, as opposed to a gradual release, which allows better monitoring of the onset of adverse reactions.

Readily available foods are the more logical choice for DBPCFC (Sampson et al., 2012). However, readily available foods may trigger subjective reactions based on taste and based on reactions classified as Oral Allergy Syndrome (OAS), rather than true allergic reactions. This leads to a false-positive DBPCFC outcome. It might also be difficult to administer a precise dose of allergen.

Up to now, there was no solution to reduce the false-positive reaction in combination with non-delayed absorption.

SUMMARY OF THE INVENTION

The invention relates to novel compositions and methods for detecting/diagnosing or treating food allergies based on the development or use of novel formulations which deliver the allergen in the stomach and allow controlled exposure or bypass of the oral cavity.

The invention may be used for the treatment of food allergies by delivering food allergens to the gut immune system without substantial exposure of the esophagus or mouth. The invention may also be used to induce tolerance to food allergens in allergic subjects by oral administration of allergens formulated to dissolve in the stomach and/or in the oral cavity (e.g., in the mouth).

The invention also provides improved reactivity tests (such as DBPCFC) with non-delayed absorption, and without taste perception. The products of the invention can readily dissolve in gastric conditions, allowing quick absorption, while the oral cavity is not exposed to allergens or the taste of the food.

An object of the invention therefore resides in a product suitable for oral administration comprising, in the form of a particle (or of particles), a food allergen and a matrix, and wherein the product dissolves in the stomach.

Another object of the invention resides in a product suitable for oral administration comprising, in the form of a particle (or of particles), a food allergen and a matrix, wherein the product releases food allergen in the stomach.

A particular embodiment of the invention resides in a product suitable for oral administration comprising, in the form of a particle (or of particles), a food allergen and a matrix, wherein the product starts to dissolve rapidly in the mouth (more than 30% of the product is dissolved in less than 2 minutes in the mouth allowing quick release of allergen) and releases food allergen in the stomach.

The product of the invention is preferably a particulate product wherein the allergen is embedded in a matrix. In a first embodiment, the food allergen forms a layer surrounding a neutral solid core. In an alternative embodiment, the food allergen and matrix are mixed as a granulate.

In a first embodiment, the product is encapsulated in a stomach-labile coating stable at neutral pH, allowing no exposure of the oral cavity and esophagus to the allergen and rapid dissolution in the stomach. Such formulations are particularly suited for food challenge or allergy diagnostic applications.

In an alternative embodiment, the product is not encapsulated or contains a fraction of the food allergen on its surface, allowing controlled exposure of the oral cavity or esophagus to the allergen. Such formulations are particularly suited for OIT applications.

Another object of the invention is a method to deliver a food allergen to the gastro-intestinal tract of a subject comprising administering to the subject a product as defined above. The method ensures controlled (e.g., fast, limited or no) exposure of the oral cavity and esophagus to the food allergen.

The invention also relates to a method to determine reactivity of a subject to a food allergen, comprising exposing said subject to said allergen via the oral route, wherein the food allergen is formulated as a product as defined above.

The invention further resides in a method for inducing tolerance to a food allergen in a subject allergic to said food allergen, the method comprising administering to said subject said food allergen by oral administration, wherein the food allergen is formulated as a product as defined above.

Still a further object of the invention is a product as defined above for use to determine reactivity of a subject to a food allergen by oral administration.

Another object of the invention is a product as defined above for use to induce tolerance to a food allergen in a subject allergic to said food allergen by oral administration.

A further object of the invention is a pharmaceutical composition comprising a product as defined above and one or several pharmaceutically-acceptable vehicles or excipients.

The invention also relates to a method for preparing a food allergen product, the method comprising (i) providing a food, (ii) optionally treating the food to enrich or purify allergens, (iii) optionally heating the food or allergens of (i) or (ii), and (iv) mixing or coating the food or allergens with a matrix to form particles.

The invention may be used in any subject, particularly human subjects, and is applicable to any food allergen such as peanut (or groundnut), milk, egg, cereals, tree nuts and seeds, fish or crustacean, or a combination thereof.

LEGEND TO THE FIGURES

The patent or application file contains at least one drawing executed in color. Copies of this patent or patent application publication, with color drawing(s), will be provided by the Office upon request and payment of the necessary fee.

FIG. 1. Composition of a formulation of the invention comprising a neutral core and no coating.

Figure 2:
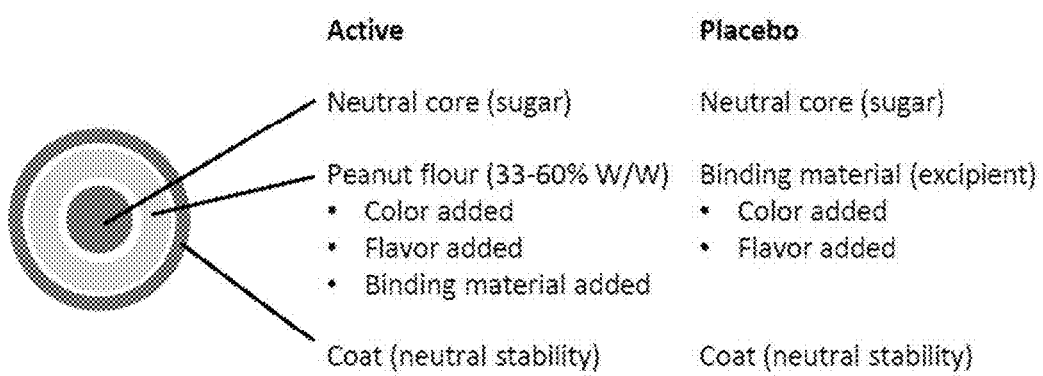

FIG. 2. Composition of a formulation of the invention comprising a neutral core and a coating.

FIG. 3. Composition of a formulation of the invention comprising a neutral core, a coating and an outer layer.

FIG. 4. Composition of a formulation of the invention comprising an allergen embedded in a matrix as a granulate.

Figure 5:
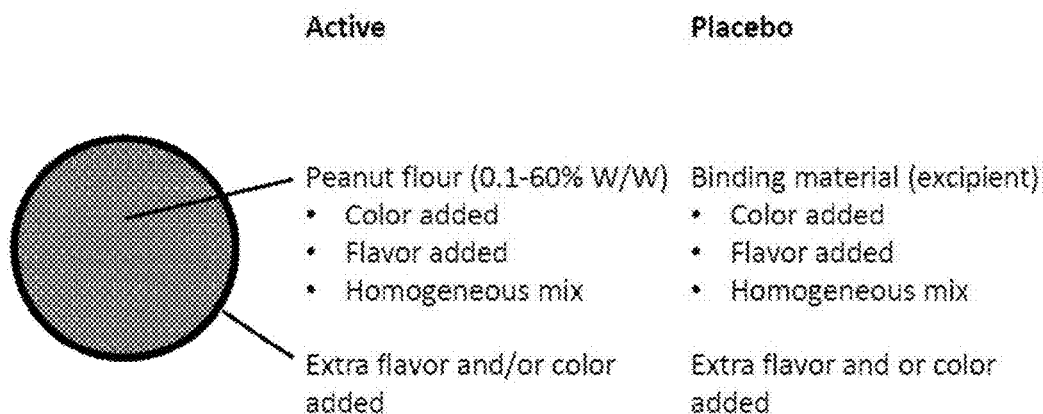

FIG. 5. Composition of a formulation of the invention comprising an allergen embedded in a matrix as a granulate and having an outer layer.

Figure 6:
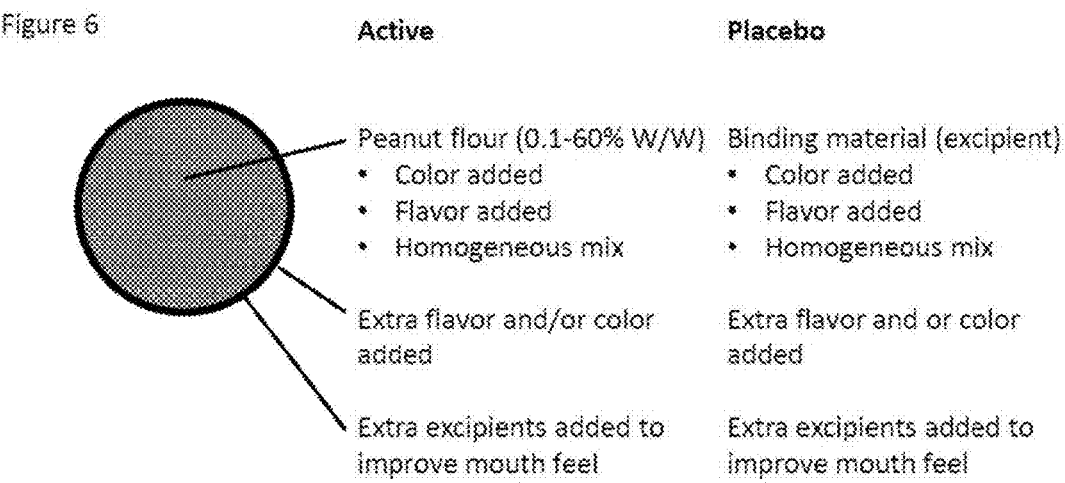

FIG. 6. Composition of a formulation of the invention comprising an allergen embedded in a matrix as a granulate and having an outer layer of extra flavoring and/or colorant and/or mouth feel-improving agent.

Figure 7:
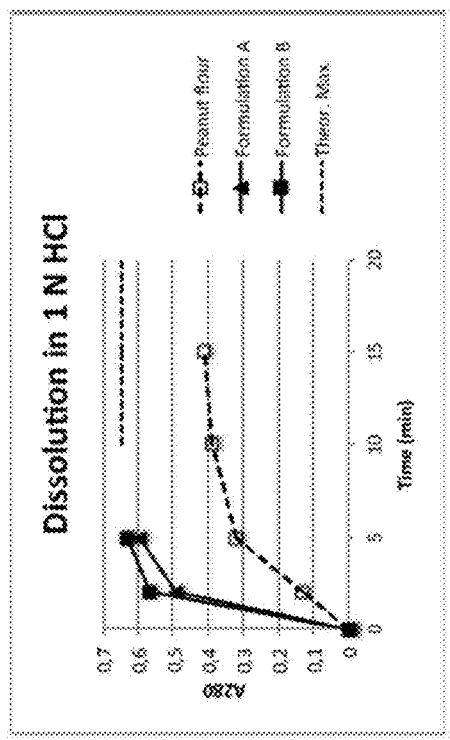

FIG. 7: Dissolution profile of formulations A and B at pH 1.

Figure 8:
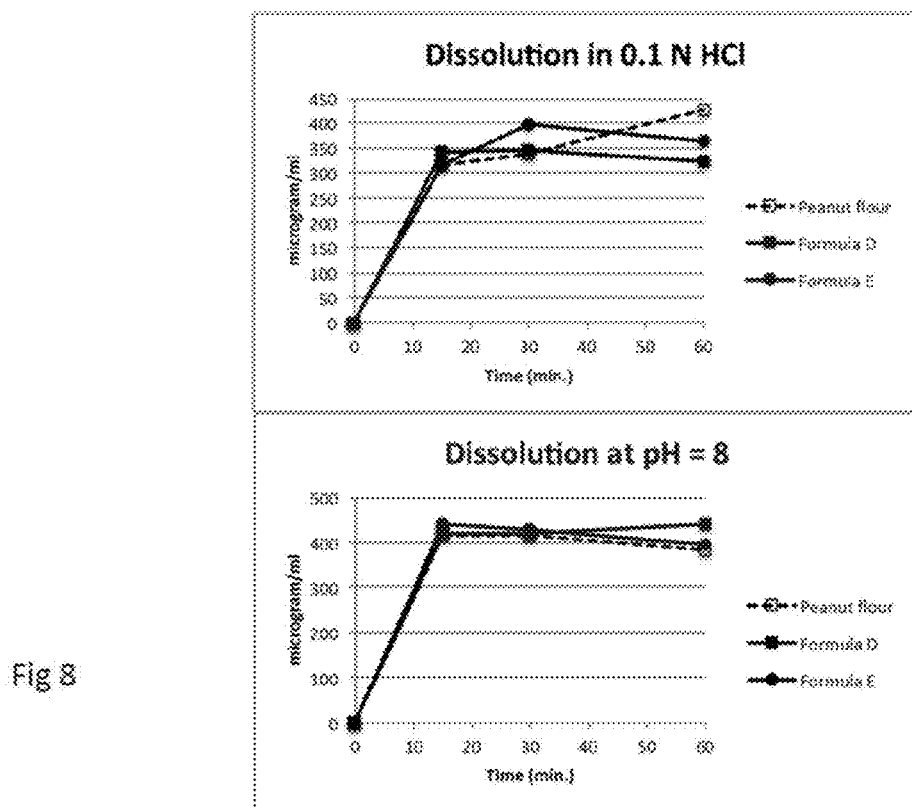

FIG. 8: Dissolution profile of formulations D and E at pH 1 or pH 8.

Figure 9:
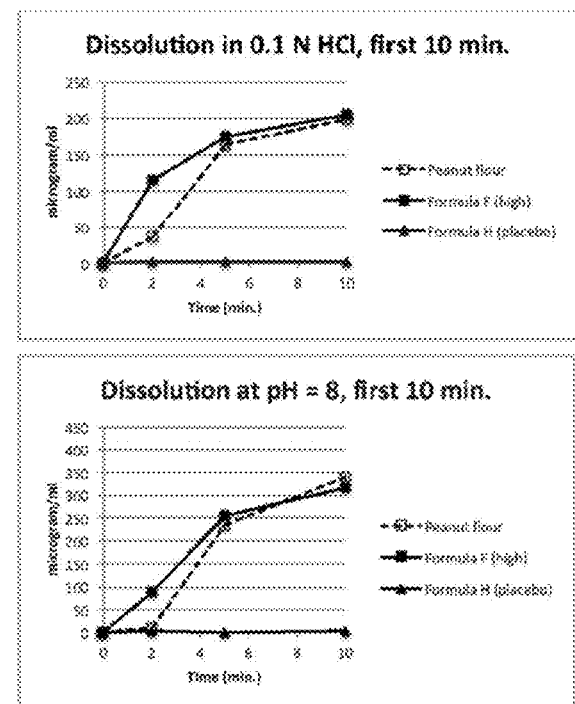

FIG. 9: Dissolution profile of formulations F and H at pH 1 or pH 8.

Figure 10:
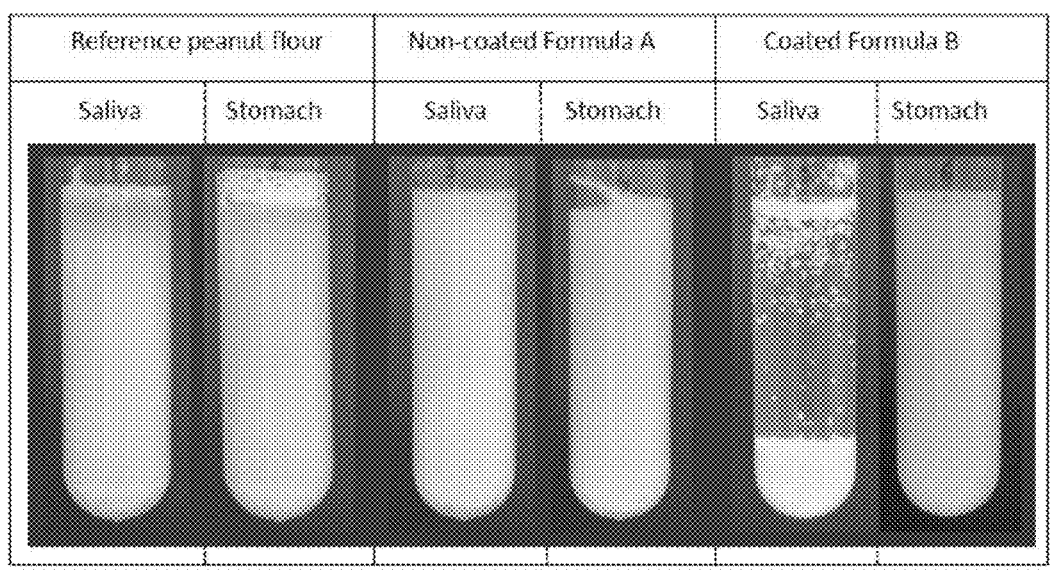

FIG. 10: Visual assessment of disintegration of granules. Left: Reference peanut flour (0.15 g in 10 ml); Middle Panel: Non-coated Formulation A (0.5 gram in 10); Right Panel: Coated Formulation B (0.5 gram in 10 ml). Formula were tested at two conditions as indicated in each Panel; Saliva: Saliva-like buffer at pH 7.6; Stomach: Stomach-like fluid at pH 1.0. Amounts of materials were chosen such that the theoretical amounts of peanut protein were approximately the same for all dissolution experiments.

FIG. 11: Kinetics of dissolution of formulations A and B at neutral and low pH, determined with BCA. A: Saliva-like buffer at pH 7.6; B: Stomach-like fluid at pH 1.0. Squares: reference peanut flour; Circles: Non-coated formulation A; Triangles: coated Formulation B.

Figure 12:
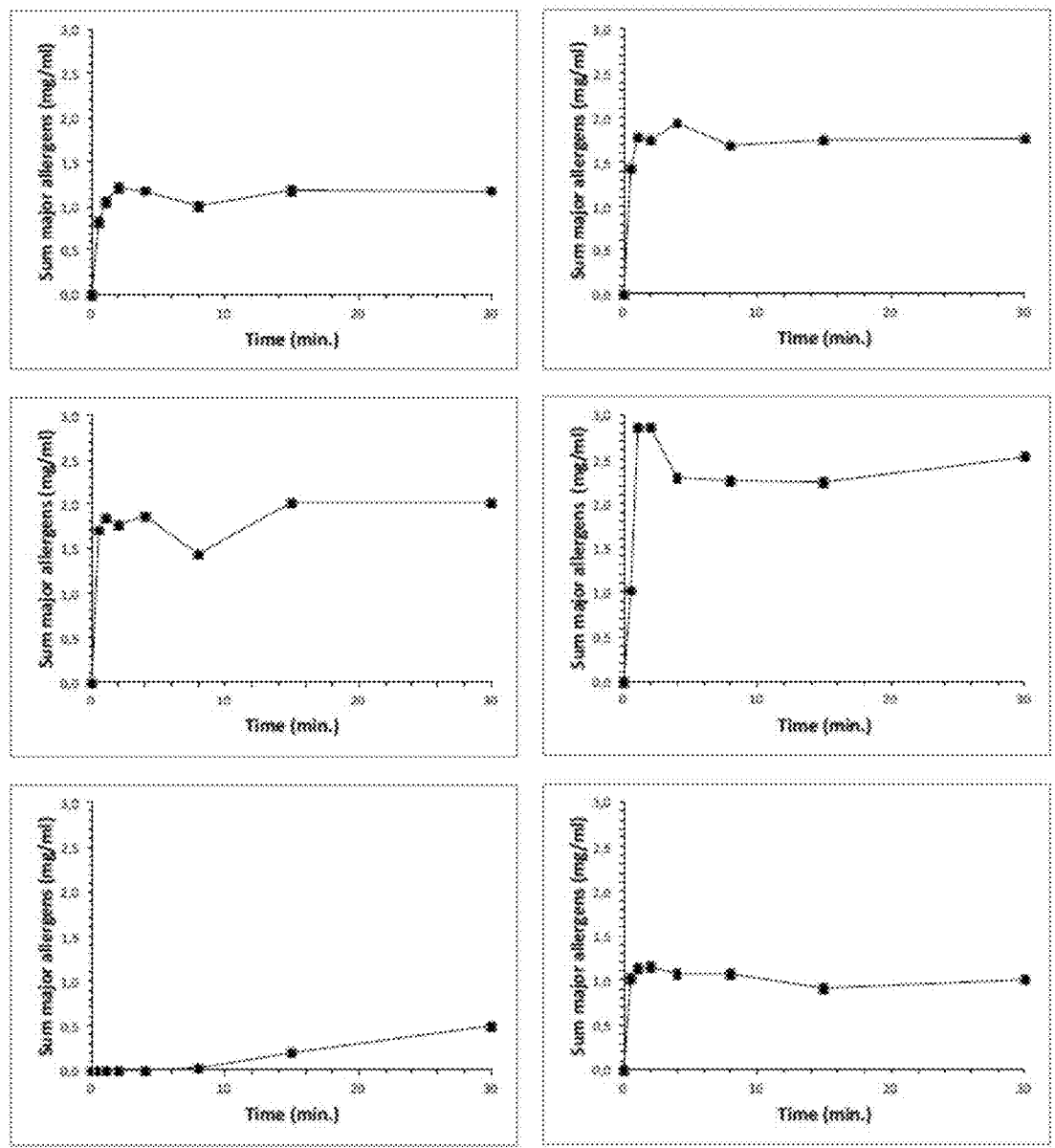

FIG. 12: Release of peanut allergens from formula in time, at neutral and low pH, as determined by SDS-PAGE. Left-hand side: dissolution at neutral pH (7.6). Right-hand side: dissolution at low pH (1.0). Upper panels: Reference peanut flour. Middle panels non-coated formula (formulation A). Lower panels: coated formula (Formulation B). On the Y-axis, the sum of the major allergens Ara h1, Ara h2, Ar ah3, and Ara h6 is shown.

Figure 13:
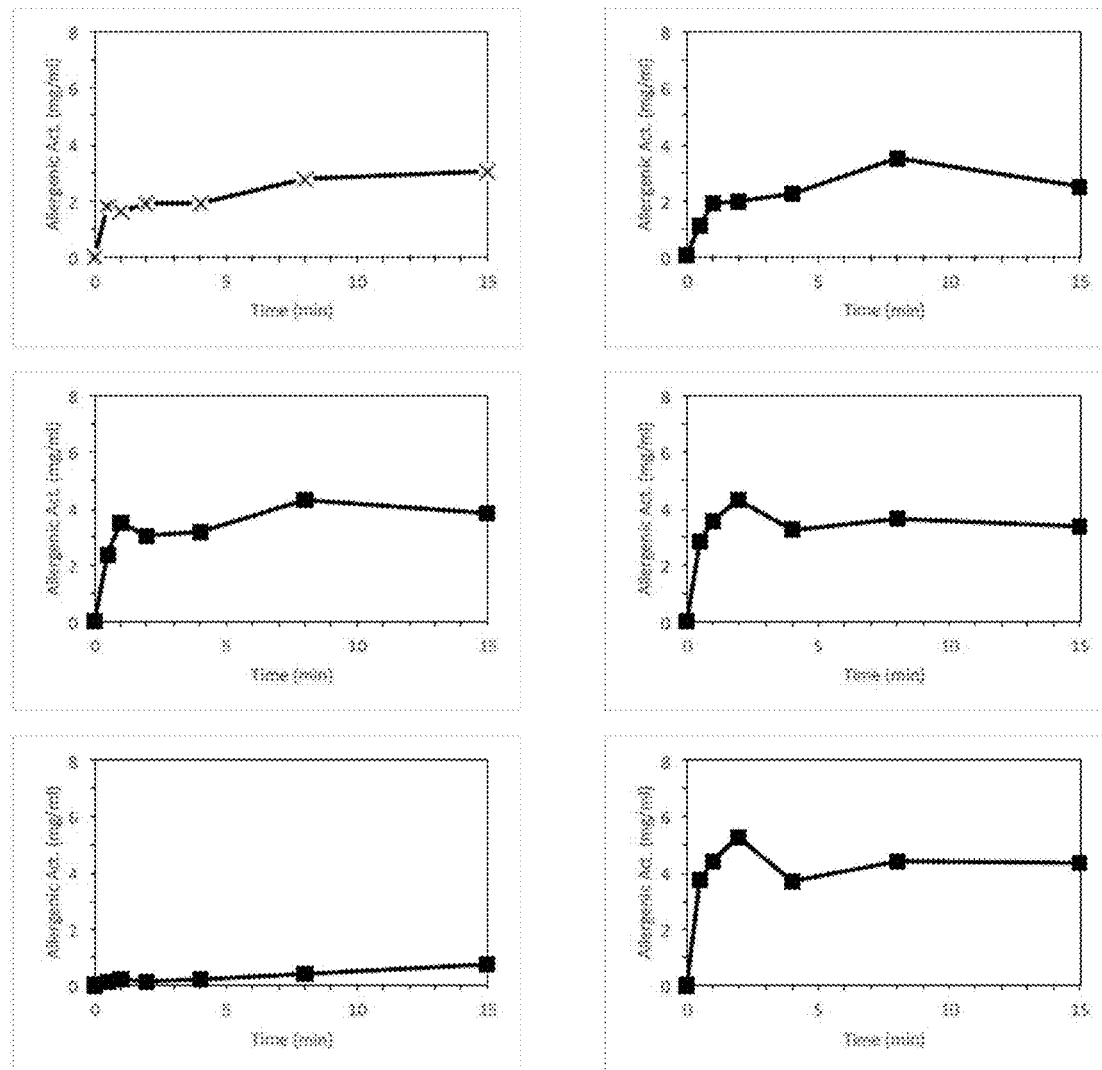

FIG. 13: Release of allergenic activity. Left-hand side: dissolution at neutral pH (7.6). Right-hand side: dissolution at low pH (1.0). Upper panels: Reference peanut flour. Middle panels non-coated formula (formulation A). Lower panels: coated formula (Formulation B). Allergenic activity is expressed in mg/ml of the protein concentration of a standard solution of reference peanut flour. The mean of two experiments is shown.

FIG. 14: Visual assessment of disintegration (60 minutes) of various formulations: Panel A: Reference peanut flour; Panel B: Formulations A, B and B6; Panel C: Formulations A3 and B3-2.

Figure 15:
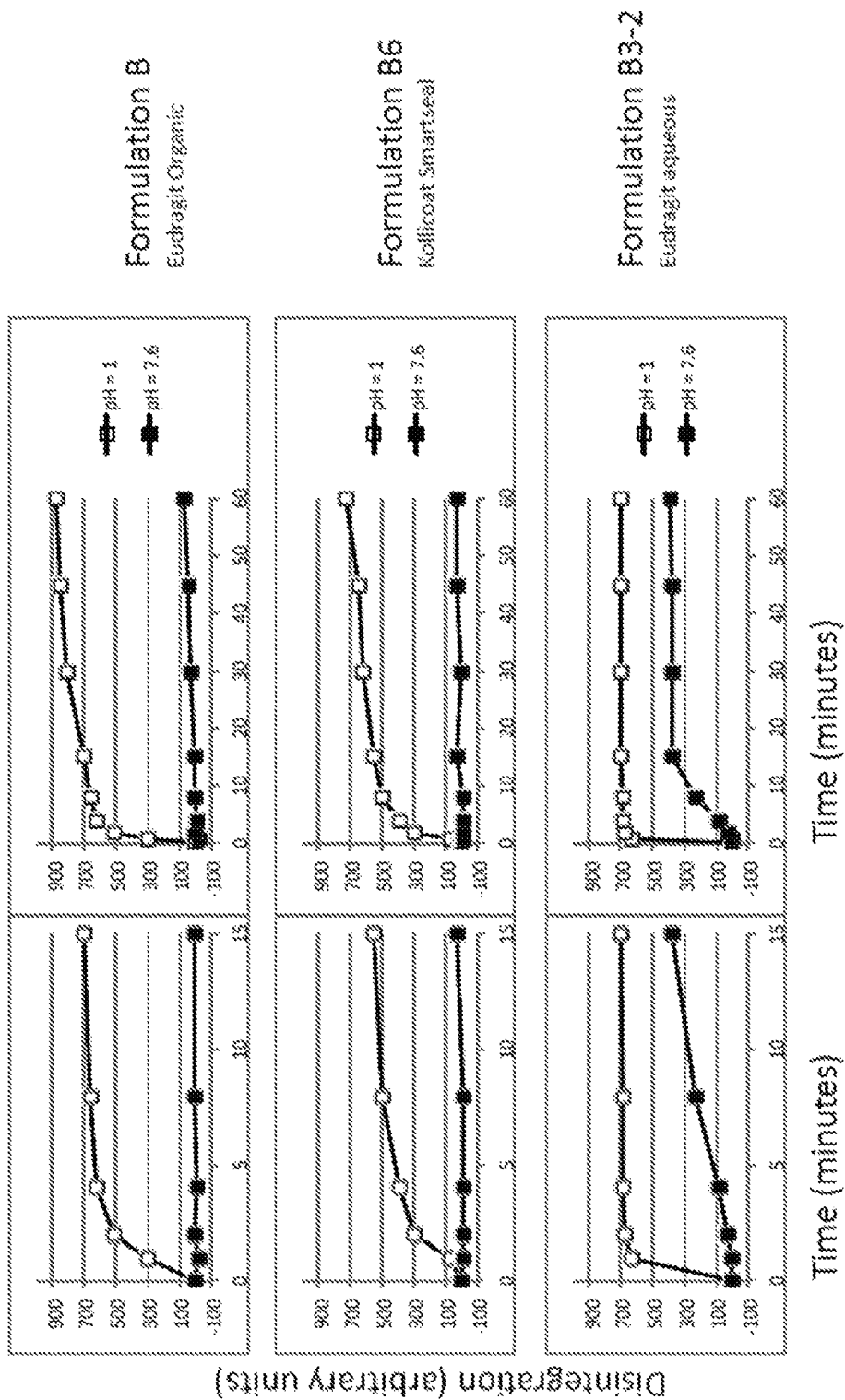

FIG. 15: Disintegration of coated Formulations, comparison of low pH (pH=1.0, open squares) and neutral pH (pH=7.6, black squares). Right: time course up to 60 min. Left: zoom-in to 15 min. Upper panels: coated formulation B; Middle panels: coated formulation B6; Lower panels: coated formulation B3-2.

DETAILED DESCRIPTION OF THE INVENTION

The invention relates to novel compositions and methods for detecting/diagnosing or treating food allergies based on novel formulations which release the allergen in the gastrointestinal tract and allow controlled taste, immunogenicity and exposure of the oral cavity. The invention provides improved reactivity tests (such as DBPCFC) with non-delayed absorption, and without the taste perception and/or with controlled taste. The product readily dissolves at gastric conditions allowing quick absorption, while the oral cavity is not exposed to allergens or the taste of the food. The invention also allows the treatment of food allergies by delivering food allergens to the gut immune system with controlled exposure of the esophagus or mouth. The invention may be used to induce tolerance to food allergens in allergic subjects by oral administration of allergens formulated according to the invention.

Many reports have been published on the induction of tolerance by exposing an allergic subject to the food in question via the oral route (Oral ImmunoTherapy, OIT). However, this form of OIT is not suitable for clinical practice because many patients develop Eosinophilic Esophagitis (EoE) (Ridolo et al., 2011; Wasserman et al., 2011; Sanchez et al., 2012), a condition that severely impacts the quality of life of allergic patients. Furthermore, while stopping OIT results in a gradual decrease of EoE symptoms, it will take 4 to 8 weeks of elimination of the food from the diet until the symptoms of EoE disappear (Spergel at al., 2005). However, for efficacious OIT, the food should be taken regularly (e.g., daily), and interrupting the daily schedule leads to a loss of the developed tolerance (Rolinck-Werninghaus et al., 2005; Nowak-Wegrzyn and Sampson, 2011). Furthermore, while conventional OIT may often only lead to a temporary lower local reactivity (i.e., a local anergy), achieving desensitization or induction of tolerance would require higher doses of offending allergens which cannot be administered orally in view of adverse clinical effects mentioned above.

US2005/063994 relates to compositions for release of microorganisms containing an immunogen to the intestine, essentially via rectal administration. WO2011/018504 relates to oil drop formulations and WO2007/112747 relates to complex formulations with separated distinct immunogens that are released in the stomach or the intestine. These documents do not address the issue of controlled exposure of oral cavity to allergens in sensitized subjects. The present invention provides novel compositions and methods allowing quick delivery of food allergens to the gut immune system with controlled taste and exposure of the esophagus to the food. The products of the invention have a defined composition, are pharmaceutically compatible, and are essentially tasteless or taste-controlled, limiting the chance of subjective adverse reactions and OAS as described above for the use in DBPCFC. Furthermore, because the exposure of the esophageal mucosa to the allergen is controlled, higher doses of allergen can be used in the product. Moreover, the risk of causing sensitization of a subject, as observed by contact of a normal allergen with the esophageal mucosa (Wassermann et al., 2011), is very limited. By controlling exposure of the esophagus to the food, the risk of Eosinophilic Esophagitis and sensitization is therefore avoided.

The invention therefore provides a substantial improvement in the administration of food allergens to allergic patients and allows improved reactivity detection and desensitization methods.

Formulation

As indicated, the invention lies, inter alia, in the development of novel formulations of food allergens with specific disintegration/dissolution profiles, which are particularly advantageous for inducing tolerance or testing reactivity to food allergens in allergic subjects. More specifically, the invention provides pharmaceutical products and compositions suitable for oral intake, comprising, in the form of particles, a food allergen and a matrix, wherein the composition dissolves under acid conditions.

The invention also provides compositions suitable for oral intake, comprising, in the form of particles, a food allergen and a matrix, wherein the composition releases food allergen in the stomach.

The invention also provides compositions suitable for oral administration comprising, in the form of particles, a food allergen and a matrix, wherein the product starts to dissolve rapidly in the mouth (more than 30% of the particles are dissolved in less than 2 minutes in the mouth) and releases food allergen in the stomach. Such dissolution profile is particularly remarkable as it is 3-5 times faster than the unformulated allergen.

In a particular embodiment, the products or particles of the invention contain a stomach-labile coating that is stable at neutral pH. Such formulations dissolve in the gastrointestinal tract but not in the oral cavity and therefore prevent exposure of the oral cavity to the allergen. Such formulations can be essentially non-immunogenic, essentially tasteless (or taste-controlled if the coating contains a defined flavoring agent), and very much adapted for food challenge tests.

In another particular embodiment, the products or particles of the invention contain an outer layer comprising a controlled amount of food allergen. Such formulations dissolve in the gastro-intestinal tract and allow limited, controlled exposure of the oral cavity to the allergen. Such compositions can start to dissolve in the mouth and can be essentially tasteless (or taste-controlled if the product contains a defined flavoring agent), and are very much adapted for OIT or allergy detection.

In another particular embodiment, the products or particles of the invention contain an outer layer comprising a controlled amount of flavoring and/or coloring and/or mouth feel improving agents. Such formulations can start dissolving quickly in the mouth allowing fast and controlled exposure of the oral cavity to the allergen. Such compositions are very much adapted for food challenges or allergy detection.

A particular product of the invention is in the form of particles comprising a neutral core surrounded by a first layer comprising the food allergen.

In another particular embodiment, the core can directly contain the food allergen without any subsequent allergen-containing layer.

Another particular product of the invention is in the form of particles comprising the food allergen embedded in the matrix, preferably as a granulate.

In a particular embodiment, the products of the invention do not contain a stomach-labile coating. Such products are not encapsulated and may allow controlled dissolution, taste and immunogenicity. In particular, a composition comprising a food allergen embedded in a matrix prepared by direct granulation provides very suitable disintegration profile. Such compositions may be further modified to include additives such as, e.g., flavoring agent(s) and/or coloring agent(s) and/or a sweetener, and/or a texturing agent, and/or an opacifier, and/or a mouth feel improver, in order to control taste and appearance. Other techniques suitable to make such granules of the invention include, without limitation, fluidized-bed granulation, compaction, or extrusion.

In another particular embodiment, the products of the invention further comprise a stomach-labile coating layer stable at neutral pH. With such composition, exposure of the oral cavity to the allergen is essentially avoided, and the product may be tasteless or taste-controlled, by incorporating a suitable additive (e.g., flavoring agent) in the coating. Such products are particularly useful for OIT and may be used as well for food challenge or allergy diagnostic/detection. Such a product is essentially non immunogenic in itself, and becomes immunogenic only upon disintegration, releasing the food allergen(s). In other words, in intact, non-disintegrated/dissolved form, the product is essentially non immunogenic because the allergen is essentially not exposed to or not in sufficient contact with the tissues, and it is only upon or during dissolution that the allergen is released and can induce immunogenic response. This aspect is important since it avoids exposure of the oral cavity to the allergens when the composition is ingested orally. The non-immunogenic character may be verified in any suitable system, such as those disclosed in the examples. In particular, by exposing the composition or product to immune cells or antibodies, it can be verified that no specific reaction develops. In a preferred embodiment, the lack of immunogenicity is verified by the absence of detectable or substantial eosinophilic response in the oral cavity.

The lack of immunogenicity is ensured in the oral cavity (mouth and esophagus) by stability of the product/composition at neutral or slightly acidic pH. The pH in the mouth is substantially neutral (i.e., between 6 and 8, more specifically between 6.5 and 7.5) and in the esophagus, the normal pH is between 4 and 6, more specifically between 4.5 and 5.5. The compositions of the invention may be engineered to be stable at such pH ranges and therefore to not dissolve in these compartments. More specifically, in a preferred embodiment, the compositions of the invention comprise a stomach-labile coating that is stable at a pH comprised between 4 and 8, typically between 6 and 8. Stability indicates that essentially no product dissolves at such pH, although a limited dissolution may not be excluded with time. In particular, a product is stable at neutral pH when, preferably, less than 10% of the product dissolves in vitro after 30 minutes in a water solution at a pH of 7, more preferably less than 5%.

By adding such a coating to the particles of the invention, essentially tasteless products can also be prepared. The lack of food taste is an advantageous feature since it avoids subjective response of the treated patient. In this regard, the term "tasteless" indicates that the product is essentially devoid of the food taste and difficult to recognize.

Alternatively, the taste of the product may be controlled by e.g., adding a flavor into the product (coating or other layers). It is thus possible to confer on the product a distinct taste, unrelated to the food, thereby masking the food taste by e.g., a dominant taste. Alternatively, it is possible to confer on the product the taste of the food in question by using an artificial flavor. In such a way, the taste/flavor may be controlled and used in a similar manner in both the product and a placebo. Examples of flavoring agents include, without limitation, orange flavor, peanut flavor, caramel flavor, vanilla flavor, banana flavor, citric acid flavor, lemon flavor, honey flavor, chocolate flavor, bubble gum flavor, or strawberry flavor. Particular examples of flavors include orange flavor (Firmenich, Switzerland), or citric acid flavor (Sigma-Fluka, Switzerland).

These compositions or products of the invention are preferably designed to dissolve under acidic conditions, preferably at a pH below 4. More preferably, under such conditions, the product dissolves rapidly, allowing fast release of the allergen. In this regard, data presented surprisingly show that food allergens may dissolve more rapidly under acidic conditions when formulated according to the invention than in free form. As shown FIG. 7, formulations A and B dissolve more rapidly than unformulated peanut flour under acidic conditions. These results were totally unexpected and provide remarkable advantages for the compositions of the invention. Without being bound by theory, one explanation would be that during formulation, the allergen is dispersed in a minimal amount of water and then mixed with the matrix or excipients. Once dried, the matrix or excipients would enable the allergen to dissolve more quickly.

Alternative compositions or products of the invention are preferably designed to start dissolving rapidly under neutral conditions, preferably at a pH of about 8. Data presented surprisingly show that food allergens may dissolve more rapidly under neutral conditions when formulated according to the invention than in free form. As shown FIG. 9, formulation H dissolves more rapidly than unformulated peanut flour under neutral conditions. These results were totally unexpected and provide remarkable advantages for the compositions of the invention. Such formulations can allow a fast initiation of dissolution in the mouth and progressive release until the stomach. Quick release of allergen in the mouth is important because at ingestion, a food is kept in the mouth for only a short time before it is transported by peristaltic movement through the esophagus into the stomach. Typically, chewing, food bolus formation, swallowing, and transportation to the stomach takes about 2 minutes.

Furthermore, the above encapsulated or non-encapsulated particulate products of the invention may further comprise an outer layer to further control the properties thereof. In this regard, the outer layer may comprise a controlled amount of food allergen, so as to initiate a controlled immune response within the oral cavity, prior to the massive release in the stomach. In particular, the outer layer may comprise from 0.5%-15% by weight of the total amount of food allergen of the product, while the first layer or granulate comprises from 99.5% to 85% by weight of the food allergen, relative to the total amount of food allergen in the product. Preferably, the outer layer, when present, comprises from 1% to 10%, even more preferably from 1 to 7% by weight of the total amount of food allergen of the product.

In addition, the outer-layer, when present, may contain one or more additives such as one or more flavoring agent(s) and/or coloring agent(s) and/or sweeteners, and/or a texturing agent, and/or opacifier(s) and/or mouth feel improving agents, so as to control taste and appearance of the product, if necessary.

Examples of flavoring agents include, without limitation, orange flavor, caramel flavor, vanilla flavor, banana flavor, citric acid flavor, lemon flavor, honey flavor, chocolate flavor, bubble gum flavor, or strawberry flavor.

Examples of coloring agents include, without limitation, Caramel (particularly suitable for peanut flour formulation since this colorant matches the color of peanut flour), Titanium dioxide (which can also serve as an opacifier), or red colorant Enocianin.

The products of the invention may be e.g., in the form of particles, powder, microgranules, microcapsules, etc.

In a particular embodiment, the product is a microcapsule or a granule containing the food allergen. Different structures of microcapsules or granules can be used, which may further comprise one or several excipients. Most preferably, the microcapsules contain (i) a core, such as a granule or a neutral core covered by a layer, wherein said core comprises the food allergen(s) and, optionally, one or several excipients, (ii) optionally, a stomach-labile coating and/or (iii) optionally, an outer layer comprising excipients, additives and/or a controlled amount of food allergen.

In a particular embodiment, the product comprises coated granules or microcapsules, obtainable by coating granules of the food allergen, with or without excipient(s), of a predefined size, with a stomach-labile coating.

In another particular embodiment, the product comprises non-coated granules or microspheres, obtainable by direct granulation of the food allergen, with or without excipient(s), with a predefined size.

In another particular embodiment, the granules of allergen are particles of a predefined size obtainable by pelleting the food allergen, with or without excipient(s), by extrusion, followed by spheronization to obtain uniform, spherical particles that can be coated with a stomach-labile coating. In another embodiment, the granules or particles of food allergen comprise a neutral core, which is first coated with the food allergen, either or not in combination with excipient(s), and subsequently coated with a stomach-labile coating.

A particular object of the invention relates to a product suitable for oral administration comprising particles having a neutral core surrounded by a first layer comprising a food allergen, and wherein the product dissolves in the stomach or releases food allergen in the stomach. An example of such a product is described in the examples as formulation A. The neutral core can be made of sugar or microcrystalline cellulose spheres, the latter being non-cariogenic and also more suitable for diabetics. In a preferred embodiment, the composition comprises (or is prepared by mixing) the following ingredients (in % by weight based on total weight of product):

| | |
|---|---|
| Allergen | 20-40%, 29-41%, such as 30-35%, |
| Povidone (binder) | 10-20%, 12-20%, such as 15-20%, |
| Core (sugar) particles | 40-60%, 42-57%, such as 45-50%, and |
| Flavor and/or colorant | 0.0-1%, such as 0.1-1%. |

Another particular object of the invention relates to a product suitable for oral administration comprising particles of a food allergen embedded in a matrix, and wherein the product dissolves in the stomach or releases food allergen in the stomach. Examples of such a product are described in the examples as formulations D and E. In a preferred embodiment, the composition comprises (or is prepared by mixing) the following ingredients (in % by weight based on total weight of product):

| | |
|---|---|
| Allergen | 50-60%, |
| Powdered sugar | 37-43%, |
| Povidone | 1-5%, and |
| Flavor and/or colorant | 0.0-1%. |

Another particular object of the invention relates to a product suitable for oral administration comprising particles having a neutral core surrounded by a first layer comprising a food allergen, and a coating layer stable at neutral pH, wherein the product dissolves in the stomach or releases food allergen in the stomach. An example of such a product is described in the examples as formulation B. In a preferred embodiment, the compositions are obtained by coating a formulation A and comprise the following ingredients (in % by weight based on total weight of product):

| | |
|---|---|
| Formulation A | 40-60% such as 53-62 or 47-57%%, |
| Coating | 25-45%, such as 33-43% (Eudragit) or 25-30 (Kollicoat), |
| Coat excipient (plasticizer) | 0.1-2%, and |
| Coat anti-adherent (e.g. talc) | 1-10%. |

Such formulations B may further comprise 0.1-3% of an anti-aggregation agent such as Aerosil200 or Syloid 72FO, to avoid agglomeration during storage, if appropriate.

Another particular object of the invention relates to a product suitable for oral administration comprising particles of a food allergen embedded in a matrix, said particles comprising an outer layer comprising a colorant and/or a flavor and/or a mouth feel improver, wherein the product releases at least 25%, more preferably at least 30% of the allergen after 2 minutes in the mouth. Examples of such a product are described in the examples as formulations F, G and H. In a specific embodiment, the invention relates to a product suitable for oral administration comprising particles of a food allergen embedded in a matrix and, said particles comprising an outer layer comprising a colorant and/or a flavor and/or a mouth feel improver, wherein the matrix comprises at least Powdered sugar, Povidone and Avicel and wherein the outer layer comprises colloidal silicon dioxide or hydroxyethyl-cellulose or a flavoring agent. In a preferred embodiment, the composition comprises (or is prepared by mixing) the following ingredients (in % by weight based on total weight of product):

| | |
|---|---|
| Allergen | 0.1-70%, |
| Powdered sugar | 35-60%, |
| Povidone K29-32 | 0-3%, |
| Avicel PH101 | 0-45%, |
| Colorant 1 | 0.1-2%, |
| Opacifier | 0.5-20%, |
| Flavor 1 | 0-0.5, preferably 0.1-0.5% |
| hydroxyethyl-cellulose | 0-2%, preferably 1-2%, and |
| colloidal silicon dioxide | 0-0.5%, preferably 0.1-0.5%. |

Another particular object of the invention relates to a product suitable for oral administration comprising particles of a food allergen embedded in a matrix, a coating layer stable at neutral pH, and wherein the product dissolves in the stomach or releases food allergen in the stomach.

Another particular object of the invention relates to a product suitable for oral administration comprising particles of a food allergen embedded in a matrix, an outer layer comprising an additive (e.g., a flavoring and/or coloring and/or a sweetener, and/or a texturing agent, and/or opacifier agent), and wherein the product dissolves in the stomach or releases food allergen in the stomach. Examples of such a product are described in the examples as formulation F.

A further particular object of the invention relates to a product suitable for oral administration comprising particles having a neutral core surrounded by a first layer comprising a food allergen, a coating layer stable at neutral pH, an outer layer comprising food allergen and an additive (e.g., a flavoring and/or coloring and/or a sweetener, and/or a texturing agent, and/or opacifier agent), wherein the product dissolves in the stomach or releases food allergen in the stomach. An example of such a product is described in the examples as formulation C.

The matrix may comprise one or several compounds, in mixture, which may be selected from pharmaceutically-compatible (co-)polymers. Examples of such polymers or co-polymers include polymers based on cellulose, (meth)acrylate, vinylic alcohol, alginate, maltodextrin, cylodextrin, gelatin, povidone, poly-ethylene glycol (PEG), xanthan gum, hydroxyethyl-cellulose, hydroxypropyl-cellulose and/or carboxymethyl cellulose (CMC). In a particular embodiment, the matrix comprises a cellulose, such as ethylcellulose, methylcellulose, carboxymethylcellulose (CMC), or hydroxypropyl-methylcellulose (HPMC). In another particular embodiment, the matrix comprises a hydrosoluble polymer (e.g., CMC or HPMC) and a non-hydrosoluble polymer (e.g., a methacrylate polymer). Preferred matrix comprises Povidone, such as Povidone K30. The results indeed show that a Povidone matrix allows very quick dissolution of the formulations under physiological conditions, faster and to a greater extent than non-formulated allergen, and also than other tested binders (Pharmacoat or PVA). The neutral core may comprise any compatible sugar or synthetic polymers known in the art. Preferred sugars include sucrose and lactose.

The stomach-labile coating material is designed to disintegrate in the stomach, and essentially not before the product reaches the stomach. It is also designed so that the product can dissolve rapidly to allow fast release of most of the allergen in the stomach. Preferably, the product dissolves at a pH below 5, typically a pH range from 1.2 to 4.5. The coating may comprise natural or synthetic (co)polymers such as, for instance, cationic (co)polymer(s), or mixtures thereof. Examples of such polymers include cationic copolymers based on dimethylaminoethyl methacrylate, butyl methacrylate, and methyl methacrylate, as well as ethylcellulose. Other examples are polyvinyl alcohol, hydroxypropyl methyl cellulose, and hydroxypropyl cellulose (HPC). Such copolymers are commercially available as, for instance, EUDRAGIT® E 12.5, Eudragit E100, Eudragit EPO or Kollicoat Smartseal (30D). In this regard, particularly preferred coatings comprise Eudragit 12.5 or Kollicoat Smartseat. As shown in the examples, such coating materials allow very stable formulations at neutral pH (essentially no dissolution during 45 minutes) and fast dissolution under acidic conditions.

Preferred release profile of the product is between 10 minutes and 2 hours after oral ingestion. With such a release profile, essentially no dissolution occurs in the oral cavity (mouth or esophagus) and essentially all of the food allergen is released in the stomach.

In a preferred embodiment, at least 50% of the product dissolves in 5 minutes at pH 1, preferably at least 60%.

As indicated above, the product or composition may comprise one or several excipients, such as carrier material, or filler, or binder, or lubricant. Examples of preferred excipients include, without limitation, starch from potato, corn, wheat or alternative sources, chemically modified starch, lactose, sucrose, sorbitol, mannitol, xylitol dextrose, xanthan gum. Specific examples of excipients include e.g., Povidone K30, Macrogol 4000, Talc Microace P-3, or Povidone K25. Typically, the food allergen is mixed with said one or several excipients and treated to form particles of a predefined (average) size.

Furthermore, as discussed above, the product (e.g., the matrix, coating or outer layer), may comprise additives such as a flavouring agent, a colouring agent, a sweetener, a texturing agent, and/or an opacifier.

The particles in the products of the invention may have various forms such as spherical, ovoid, geometric, etc. Furthermore, in a preferred embodiment they have a (an average) size comprised between 1 μm and 10 mm, preferably between 10 μm and 1.5 mm, most preferably between 50 μm and 1000 μm, even more preferably between 50 μm and 900 μm. Illustrative ranges of sizes are 400-600 μm; 180-250 μm or 250-355 μm. Small particles (180-250 μm) appear very well tolerated with a very good mouthfeel.

In a particular embodiment, the product of the invention comprises a solid neutral core, a first layer covering the solid core, and a coating covering the first layer. The core is preferably spherical, with an average diameter of about 90-1000 μm. The core can be made of any compatible material such as polyhydroxylated compounds or sugar(s) (e.g. lactose, saccharose, mannitol, cellulose, etc.). The first layer comprises the food allergen and, optionally, one or more excipients and/or additives. The first layer is preferably homogeneous and covers the entire surface of the core. The coat shall also be homogeneous and covering the entire surface of the first layer. The coat typically represents from 0.5 to 20%, preferably from 1 to 15% of the dry weight of the product.

Depending on the usage, the food allergen content of the products may represent from 0.1 to 99.5% by weight of the products. Particular products of the invention comprise from 40% to 95% by weight of food allergen, for instance from 40 to 70% (high dosage products), relative to the total weight of the products. Further particular products of the invention comprise from 0.1% to 5% by weight of food allergen (low dosage products), relative to the total weight of the products. Accordingly, the ratio of food allergen/matrix and excipients and additives may range from 0.01 to 100, depending on the allergen dosage.

Preferred formulations of the invention are granules or particles comprising (i) a neutral sugar core surrounded by (ii) a first layer comprising a food allergen and a binder and (iii) a coating layer stable at neutral pH. The neutral core preferably comprises sucrose or lactose. The binder preferably comprises Povidone, and the layer preferably comprises a copolymer such as Eudragit or Kollicoat Smartseal. Preferred formulations of the invention comprise the following constituents:

Non-Coated Formulations:

| Components | Amount (g) |
| --- | --- |
| Light roasted peanut flour | 275-325 |
| Povidone K30 (binder) | 120-160 |
| Core (sucrose) particles (400-600 μm) | 400-450 |

| Components | Amount (g) |
| --- | --- |
| Light roasted peanut flour | 275-325 |
| Povidone K30 (binder) | 120-160 |
| Core (sucrose) particles (180-250 μm) | 400-450 |

| Components | Amount (g) |
| --- | --- |
| Light roasted peanut flour | 275-325 |
| Povidone K30 (binder) | 120-160 |
| Core (lactose) particles (250 μm) | 400-450 |

| Components | Amount (g) |
| --- | --- |
| Light roasted peanut flour | 275-325 |
| Pharmacoat 603 (binder) | 80-90 |
| Core (sucrose) particles (250-355 μm) | 400-450 |

| Components | Amount (g) |
| --- | --- |
| Light roasted peanut flour | 200-230 |
| PVA 10-98 (binder) | 10-20 |
| Core (sucrose) particles (250-355 μm) | 270-320 |

Coated Formulations

| Components | Amount (g) |
| --- | --- |
| Light roasted peanut flour | 200-216 |
| Povidone K30 (binder) | 87-106 |
| Core (sucrose) particles (400-600 μm) | 292-298 |
| Eudragit E 12.5% (coat) | 400-430 |
| Macrogol (coat excipient, platicizer) | 3-6 |
| Talc (micronized) (coat excipient, anti-adherent to avoid sticking of granules) | 24-28 |

| Components | Amount (g) |
| --- | --- |
| Light roasted peanut flour | 200-216 |
| Povidone K30 (binder) | 87-106 |
| Core (sucrose) particles (180-250 μm) | 292-298 |
| Eudragit E 12.5% (coat) | 400-430 |
| Macrogol (coat excipient, platicizer) | 3-6 |
| Talc (micronized) (coat excipient, anti-adherent to avoid sticking of granules) | 24-28 |

| Components | Amount (g) |
| --- | --- |
| Light roasted peanut flour | 173-208 |
| Povidone K30 (binder) | 75-103 |
| Core (lactose) particles (250 μm) | 252-289 |
| Eudragit E 12.5% (coat) | 350-400 |
| Macrogol (coat excipient, platicizer) | 3-10 |
| Talc (micronized) (coat excipient, anti-adherent to avoid sticking of granules) | 22-28 |

| Components | Amount (g) |
| --- | --- |
| Light roasted peanut flour | 173-208 |
| Povidone K30 (binder) | 75-103 |
| Core (lactose) particles (250 μm) | 252-289 |
| Eudragit E PO (coat) | 350-400 |
| Sodium lauryl sulfate | 3-10 |
| Stearic acid | 10-20 |
| Talc (micronized) (coat excipient, anti-adherent to avoid sticking of granules) | 22-28 |

| Components | Amount (g) |
| --- | --- |
| Light roasted peanut flour | 200-216 |
| Povidone K30 (binder) | 87-106 |
| Core (sucrose) particles (400-600 μm) | 292-298 |
| Kollicoat Smartseal 30D (coat) | 250-300 |
| Talc (micronized) (coat excipient, anti-adherent to avoid sticking of granules) | 40-45 |
| Dibutyl sebacate | 5-10 |

Specific examples of coated formulations of the invention are described in the examples and include formulations B1, B2, B3-1, B3-2, B4, B5 and B6.

For preparing the product, a wide variety of techniques are known in the art, for example as reviewed by Thoke, 2012. In particular, microencapsulation may be performed by physical, physicochemical, or chemical techniques. Examples of physical techniques include centrifugal extrusion, pan-coating, spray-drying, mixed flow or vibrational nozzle, electro-drawing, electro-spraying, blow-drawing, or blow-spraying. Examples of physicochemical techniques include coacervation and ionotropic gelation. Examples of chemical techniques include polymerization or solvent evaporation.

Alternative to coating, granules may be made by formulating the food allergen with suitable excipient(s) followed by extrusion either or not in combination with spheronization. Such particles, without a specific coat, may still have disintegration properties as described above for coated particles because of the disintegration characteristics of the selected excipients.

A further object of the invention also resides in a method for preparing a product or composition as defined above, the method comprising:
(i) providing a food allergen,
(ii) optionally treating and/or heating the food allergen,
(iii) optionally combining the food allergen with one or more excipients or additives,
(iv) formulating the food allergen as particles having an average size comprised between 10 μm and 1 mm,
(v) optionally coating the particles of (iv) with a stomach-labile coat, and
(vi) optionally adding an outer layer to the particles of (iii) or (iv), said outer layer comprising excipient(s) and/or additive(s) and/or a controlled amount of food allergen.

In a particular embodiment, the food allergen is suspended in a solution, excipients are optionally added, the solution produced is subjected to electro-drawing or electro-spraying or blow-drawing or blow-spraying, to form microencapsulated food allergen products having a predefined average size and disintegration profile.

As discussed above, the matrix is typically a polymeric substance or mixture thereof. Also, the matrix may comprise a flavour, which may or not be the flavour of the formulated food. For instance, for peanut, the product may comprise orange flavor, peanut flavor, caramel flavor, vanilla flavor, banana flavor, citric acid flavor, lemon flavor, honey flavor, chocolate flavor, bubble gum flavor, or strawberry flavor.

In a particular embodiment, where the food is peanut, the food allergen may not need to be combined with an excipient since peanut allergen comprises endogenous carbohydrates, fibers, and proteins that can play the excipient role. The peanut allergen may be coated using the techniques described above, or the coat may be omitted in cases where the peanut material is combined with excipient having the desired disintegration properties. The peanut allergen may be heated, prior to formulation, to direct the characteristics of the peanut in terms of stability, allergenicity, and digestibility. Heat treatment may be between 60 and 180° C., preferably between 80° C. and 150° C., more preferably between 100° C. and 130° C., most preferably between 110 and 125° C., by means of roasting, boiling, or frying, for time periods between 15 minutes and 24 hours, typically between 0.5 and 5 hours, such as 1 hr, 2 hrs, 3 hrs or 4 hrs.

A further object of the invention is a method for preparing a placebo product, which method comprises:
(i) providing one or more excipients,
(ii) formulating the excipient(s) as particles having an average size comprised between 10 μm and 1 mm, and
(iii) optionally coating the particles of (ii) with a stomach-labile coat, and
(iv) optionally adding an outer layer to the particles of (ii) or (iii), said outer layer comprising excipient(s) and/or additive(s).

In a particular embodiment, the excipient(s) used is the same as for preparing the food allergen product. Furthermore, in a preferred embodiment, the matrix comprises a flavour, which is the same as that included in the food allergen product.

A further object of the invention is a composition comprising several products as defined above and one or more vehicles.

Kit

A further object of the invention is a kit comprising one or more products or compositions as described above and a container or leaflet or instruction manual. The kit may further comprise a packaging means, such as a blister, bottle, set of volumetric spoons, box, etc.

A particular kit of the invention comprises several products of the invention, having the same dose of food allergen.

Another kit of the invention comprises two separate containers, one comprising one or several products as defined above, the other comprising corresponding placebo products, wherein the food allergen component is replaced by an excipient, such that the active formulation is essentially indistinguishable from the placebo.

Food Allergen

The invention may be used with any food or food allergens such as, without limitation, groundnut, peanut, milk, egg, tree nuts and seeds (such as, but not limited to, hazelnut, cashew, walnut, pecan, Brazil nut, macadamia, chestnut, pistachio, coconut, almond, sesame, mustard), fish, shellfish, crustaceans, cereals (such as, but not limited to, wheat, corn, oat, barley, rye, rice, sorghum, spelt), legumes (such as, but not limited to, soy, kidney bean, black bean, common bean, chickpea, pea, cow pea, lentils, lupine), or mixtures thereof.

The term "food" designates the entire, intact food, or preparations or extracts thereof. The food may be in native form, raw, or cooked, or heated, or cut, or blended or mixed, for example.

The term "allergen" refers to any immunogenic molecule involved in an allergic reaction contained in food. The allergen may be of various types, such as a lipid, protein, peptide, polypeptide, etc. In a particular embodiment, the allergen is a native food preparation, a food extract, or a purified protein, polypeptide and/or peptide composition. The allergen may be in a natural state, or produced artificially (e.g., by recombinant and/or enzymatic techniques, and or de novo synthesis). The allergen may be structurally altered or modified to improve its stability, immunogenicity, etc. The allergen may be pure or in admixture with other constituents. The allergen may be a mixture of several molecules (e.g., an extract). The allergen may be used in different states, such as liquid or dry. The allergens may be in an entire, native form, or in a fragmented, denatured form, etc. A preparation is typically used, comprising several allergens as a combination, and/or allergen(s) as conjugates or complexes.

In a particular embodiment, the food allergen is raw or native food, or an extract thereof.

In another particular embodiment, the food allergen is a heated food or food extract. In this regard, the food may be treated by heating under conditions sufficient to release, denature and/or unmask allergens. In a particular embodiment, the food or extract thereof is treated at a temperature comprised between 60° C. and 180° C. Some allergen preparations may be subjected to a mild heat treatment of between 70 and 110° C., generally between 70 and 80° C., or a higher treatment of between 100 and 180° C. Also, the duration of heat treatment can be varied: if heating temperatures are limited (for example due to known denaturation at certain temperatures) an extended duration of heating at a somewhat lower temperature may be applied. Preferably, the food or extract thereof is treated at a temperature comprised between 80° C. and 150° C., more preferably between 100° C. and 130° C., most preferably between 110 and 125° C., for a period of time between 15 minutes and 24 hours, typically between 0.5 and 5 hours, such as 1 hr, 2 hrs, 3 hrs or 4 hrs.

Allergen preparations may also be roasted, or grilled, or lyophilized, or floured.

The extract is any preparation obtained or derived from an entire food, which is enriched in allergen. The extract may be lysate, concentrate or fraction of a food. Preferably, the extract is enriched in allergenic proteins.

In another embodiment, the food allergen is a purified allergen.

In a preferred embodiment, the food is peanut. A preferred peanut allergen preparation for use in the invention is roasted peanut, peanut flour, or an extract thereof. The peanut allergen may be heated at a mild temperature and/or treated or selected for low fat content. Peanuts contain up to 40% fat. Peanut flours are normally prepared by cold-pressing, resulting in about 20% fat. Low fat flours for use in the invention are flours with a fat content below 20%, preferably below 15%, even more preferably of 12% fat or less. By extensive defatting, values as low as 5% can be achieved, even an essentially fat-free flour (e.g., 0.1 to 1% fat). Specific examples of low-fat flours are flours with a fat content of 15%, 12%, 7%, 5% or 2%. The invention shows that peanut preparation with low fat content and subjected to mild heat treatment provides surprising release and reactive effects when formulated according to the invention.

Alternatively, the peanut allergen may be a preparation enriched for peanut allergens (such as Ara h1, Ara h2, Ara h3, Ara h4, Ara h5, Ara h6, Ara h7, Ara h8, Ara h9, Ara h10, Ara h11, Ara h12, Ara h13, Ara h14, Ara h15, Ara h16, or Ara h17), or fragment thereof, or isolated or purified peanut allergens or fragments thereof.

In another preferred embodiment, when the food is milk, a preferred milk allergen preparation for use in the invention is raw milk, sterilized (e.g., pasteurized) milk, dried milk powder, whey powder, casein powder, or an extract thereof. Alternatively, for milk, the allergen may be a preparation enriched in whey protein, beta-lactoglobulin, alpha-lactalbumin, and/or casein, or a fragment thereof, or isolated or purified milk allergens of fragments thereof.

In yet another preferred embodiment, when the food is egg, a preferred egg allergen preparation for use in the invention is raw egg, sterilized (e.g., pasteurized) liquid egg, dried egg powder, egg yolk powder, egg white powder, or an extract thereof. Alternatively, for egg, the allergen may be a preparation enriched in ovalbumin, ovomucoid, lactoferrin, and/or lysozyme, or a fragment thereof, or isolated or purified egg proteins or fragments thereof.

In a preferred embodiment, the food allergen is used or administered without an adjuvant. However, although not preferred, the allergen may be combined with an adjuvant, i.e., any substance that e.g., activates or accelerates the immune system to cause an enhanced immune response. Examples of adjuvants include mineral salts, such as calcium phosphate, aluminium phosphate and aluminium hydroxide; immunostimulatory DNA or RNA, such as CpG oligonucleotides; proteins, such as antibodies or Toll-like receptor binding proteins; saponins e.g. QS21; cytokines; muramyl dipeptide derivatives; LPS; MPL and derivatives including 3D-MPL; GM-CSF (Granulocyte-macrophage colony-stimulating factor); imiquimod; colloidal particles; complete or incomplete Freund's adjuvant; Ribi's adjuvant; or bacterial toxin.

Method of Testing Reactivity

Another aspect of the present invention relates to the use of a product or composition of the invention for testing reactivity of a subject to a food allergen, for diagnosing/detecting an allergy, or for testing the reactivity of a subject in the framework of a clinical study to treat food allergy or routine clinical intervention to treat food allergy.

Typically, the invention relates to an in vivo provocation test, comprising orally administering to a subject an effective amount of a product as defined above and measuring the immune reaction. Preferably, the method is done in a double blinded, placebo-controlled fashion (DBPCFC). Because the product allows controlled exposure of oral cavity and may mask or control the taste of the food allergen, the method avoids any subjective or adverse response.

The invention also relates to a method to determine reactivity of a subject to a food allergen, comprising exposing said subject to said allergen via the oral route, wherein the food allergen is in a formulation that ensures controlled exposure of the oral cavity and dissolves in the gastro-intestinal tract.

The invention also relates, generally, to a method for administering to a subject a food allergen, comprising administering the food allergen orally in a formulation that dissolves in the stomach or releases allergen in the stomach and allows controlled exposure of the mouth and esophagus.

In the method for testing reactivity, doses comprised between 0.1 mg and 10 g of the product are typically administered, once or repeatedly. Typically, escalating doses are used, for instance from 1-50 mg at the beginning until 2-5 g. Such dosages may be adjusted by the practitioner depending on the subject's status and response.

The method typically comprises a step of measuring or observing or monitoring the reaction of the subject to the administration, such a reaction being indicative of an allergic and reactive subject.

Method of Inducing Tolerance

Another aspect of the present invention relates to the use of a product or composition of the invention for inducing tolerance in (or for desensitizing) patients allergic to a food. Many reports have been published on the induction of tolerance by exposing an allergic subject to food via the oral route (Oral Immunotherapy, OIT). However, as explained before, these approaches are not suitable for clinical practice because many patients develop Eosinophilic Esophagitis and/or oral reactions. The present invention overcomes the drawbacks of the prior art techniques and allows effective desensitization by oral administration.

The method typically comprises repeated administrations of the product to induce progressive tolerance or desensitization of the allergic patient. During treatment, the dose of food allergen ingested may be adjusted. Typically, doses of food allergen comprised between 0.1 mg and 10 g, more preferably between 1 mg and 3 g may be taken orally. Generally, the protocol comprises progressively escalating doses, which may be taken on a daily basis, or every other day. The treatment may be maintained for several months or years, until a tolerance is observed in the subject. Tolerance or desensitization may be verified by a provocative test.

In a first phase of the treatment, the most suitable dose of the product may be determined, by using different, e.g., increasing amounts of product. Subsequently, the optimal dose can be maintained during treatment, and regularly adjusted. Repeated administration for several months of the allergen results in release of mediators of the immune response which influence the reaction of the immune cells in the sense of tolerance. The treatment may be considered completed and successfully conducted when reactivity to the allergen will have disappeared or will have been reduced very significantly. The success of the cure may be confirmed by an oral elicitation test, or by any other means recognized in allergology. Accordingly, the duration of the cure is variable and depends on the evolution of the clinical reactivity to the allergen.

The method may be used in allergic patients that have received a first immunotherapy of allergy, particularly a first epicutaneous immunotherapy. Such combination therapy provides further substantial advantages. This is particularly important for subjects who have difficulties starting OIT due to gastro-intestinal allergic reaction. In such cases a subject could start with subcutaneous, sublingual or epicutaneous immunotherapy and, after having reached an allergic state that allows OIT, switch to OIT according to the invention, or initiate an alternative immunotherapy with OIT according to the invention.

Further aspects and advantages of the invention will be disclosed in the following Examples section, which is illustrative of the invention.

The following non-limiting embodiments are also contemplated:

1. A pharmaceutical product suitable for oral administration comprising particles of a food allergen and a matrix, wherein said particles have a size or average size comprised between 1 µm and 10 mm and wherein the product releases allergen in the stomach.

2. The product of embodiment 1, wherein the particles comprise a neutral core surrounded by a first layer comprising the food allergen.

3. The product of embodiment 2, wherein the particles further comprise a stomach-labile coating layer stable at neutral pH.

4. The product of embodiment 2 or 3, wherein the particles further comprise an outer layer, wherein the outer layer comprises from 0.5-15% by weight of the food allergen and the first layer comprises from 99.5 to 85% by weight of the food allergen, relative to the total amount of food allergen in the particles.

5. The product of any one of embodiments 2 to 4, wherein the first layer and the outer-layer, when present, contain one or more additives preferably selected from a flavoring agent, a coloring agent and/or an opacifier.

6. The product of embodiment 1, wherein the food allergen is embedded in said matrix.

7. The product of embodiment 6, which is obtained by direct granulation of the food allergen with the matrix.

8. The product of embodiment 6 or 7, which further comprises an outer-layer.

9. The product of any one of embodiments 6 to 8, wherein the matrix and the outer-layer, when present, contain one or more additives preferably selected from a flavoring agent, a coloring agent, a sweetener, a texturing agent and/or an opacifier.

10. The product of any one of the preceding embodiments, wherein said particles have a size or average size comprised between 10 µm and 1.5 mm, preferably between 50 µm and 1000 µm.

11. The product of any one of the preceding embodiments, wherein said particles are essentially spherical.

12. The product of embodiment 1, wherein at least 50% of the particles dissolve in 5 minutes at pH 1, preferably at least 60%.

13. The product of embodiment 3, wherein the particles do not dissolve in the oral cavity.

14. The product of embodiment 1, wherein the particles dissolve in the oral cavity, particularly in the mouth, and release the allergen.

15. The product of any one of the preceding embodiments, wherein the matrix comprises one or several pharmaceutically-compatible (co-)polymers, preferably selected from sugars, (co-)polymers based on cellulose, (meth)acrylate, alginate, maltodextrin, cylodextrin, gelatin, polydone, polyethylene glycol (PEG), and/or xanthan gum.

16. The product of embodiment 15, wherein the matrix comprises cellulose, ethylcellulose, methylcellulose, carboxymethylcellulose (CMC) or hydroxypropylcellulose (HPMC).

17. The product of embodiment 15, wherein the matrix comprises a hydrosoluble polymer (e.g., CMC or HPMC) and a non-hydrosoluble polymer (e.g., a methacrylate polymer).

18. The product of embodiment 2, wherein the neutral core is essentially spherical, with a diameter of about 90-1000 μm, and preferably comprises a polyhydroxylated compound or a sugar, the first layer comprises from 70 to 100% by weight of the total amount of food allergen of the product and, optionally, one or more additive(s) and excipient(s), said layer being preferably homogeneous and covering the entire surface of the core, and a coating covering the entire surface of the first layer, which is stable at neutral pH and dissolves at acidic pH.

19. The product of any one of the preceding embodiments, wherein the food allergen is a food extract or an isolated or purified food allergen or a mixture thereof.

20. The product of any one of embodiments 1 to 19, wherein the food allergen is a heat-treated food allergen, preferably at a temperature comprised between 100 and 130° C.

21. The product of any one of embodiments 1 to 19, wherein the food allergen is a low fat allergen preparation.

22. The product of any one of the preceding embodiments, wherein the food is selected from groundnut, peanut, milk, egg, tree nuts and seeds, fish, shellfish, crustaceans, cereals, legumes, or a combination thereof, preferably peanut.

23. The product of embodiment 22, wherein the food allergen is a peanut flour preparation.

24. A pharmaceutical composition comprising a product of any one of embodiments 1 to 23.

25. A product of any one of embodiments 1 to 23, for use to deliver a food allergen to a subject by oral administration to the subject.

26. A product of any one of embodiments 1 to 23, for use to determine reactivity of a subject to a food allergen.

27. A product of any one of embodiments 1 to 23, for use to induce tolerance to a food allergen in a subject allergic to said food allergen.

EXAMPLES

Example 1. Food Allergen Formulations

Specific products according to the invention are described below.
Lactose core 1 g
Peanut allergen 1 g
HPMC 150 mg
Saccharose core 1 g
Peanut allergen 1 g
HPMC/methacrylate 150 mg
Peanut allergen 2 g
HPMC 200 mg Example 2. Preparation of Formulation A The composition of Formulation A is depicted in the following table.

| Components | Amount (g) | % wt relative to total wt |
|---|---|---|
| Light roasted peanut flour | 350-365 | 30-35% |
| Povidone K30 (binder) | 170-180 | 15-20% |
| Core (sugar) particles (250-355 μm) | 490-530 | 45-50% |
| Caramel aroma | 2-5 | 0.1-0.5% |

Peanut flour is suspended in a suitable volume of water and Povidone and caramel flavor are added under stirring until complete dissolution. The resulting suspension is sprayed onto the sugar cores in a suitable fluidized bed device (Glatt GPCG-1) equipped with a bottom spray insert, with the following process parameters:
Inlet temperature: 60° C.
Product temperature: 37° C.
Air volume: 80 m$^3$/h
Spraying pressure: 2.5 bar
Spraying rate: 11 g/min.

Example 3. Preparation of Formulation B

The composition of Formulation B is depicted in the following table.

| Components | Amount (g) | % wt relative to total wt |
|---|---|---|
| Formulation A | 520-560 g | 55-60% |
| Eudragit E 12.5% (coat) | 360-380 g | 37-42% |
| Macrogol (coat excipient, platicizer) | 3-6 g | 0.1-1.0% |
| Talc (micronized) (coat excipient, anti-adherent to avoid sticking of granules) | 20-25 g | 1-5% |

Talc is dispersed in a suitable volume of acetone-isopropanol mixture and the suspension is homogenized (for example with Ultra-Turrax homogenizer). Macrogol is dissolved in a suitable volume of water and the resulting solution is mixed with the Eudragit solution. The talc suspension is added under stirring and the resulting suspension is filtrated through a suitable stainless steel mesh screen and then sprayed onto the spheres obtained at stage A in a suitable fluidized bed device (Glatt GPCG-1) equipped with a bottom spray insert, with the following process parameters:
Inlet temperature: 36° C.
Product temperature: 31° C.
Air volume: 90 m3/h
Spraying pressure: 2.5 bar
Spraying rate: 12 g/min.

Example 4. Preparation of Formulations D and E

The composition of Formulations D and E is depicted in the following tables.
Formulation D

| Components | Amount (g) | % wt relative to total wt |
|---|---|---|
| Light roasted peanut flour | 240-260 | 50-60% |
| Powdered sugar | 170-190 | 37-43% |
| Povidone K29-32 (excipient, binder) | 12-17 | 1-5% |

Formulation E

| Components | Amount (g) | % wt relative to total wt |
|---|---|---|
| Light roasted peanut flour | 240-260 | 55-65% |
| Powdered sugar | 170-190 | 35-45% |

Povidone is dissolved in a suitable volume of water. Peanut flour and sugar are mixed in a Stephan UMC-5 mixer during 5 minutes at 300 rpm and further granulated with or without the Povidone solution during 5 minutes at 900 rpm. The resulting granules are forced through a stainless steel screen of 1.6 mm mesh size and dried in a fluidized bed dryer (Retsch) during 60 minutes at 45° C. Once dried, the granules are forced through a stainless steel screen of 0.8 mm mesh size.

Example 5. Preparation of Formulations F, G, and H (FIG. 6)

The composition of Formulations F, G, and H is depicted in the following tables.

Formulation H: Placebo

| Components | Amount | % (W/W) |
|---|---|---|
| Light roasted peanut flour | 0 | 0 |
| Powdered sugar | 500-600 | 50-60 |
| Povidone K29-32 | 20-30 | 2-3 |
| Avicel PH101 | 400-450 | 40-45 |
| Colorant 1 | 10-20 | 1-2 |
| Flavor 1 | 1-5 | 0.1-0.5 |
| Flavor 2 | 0-5 | 0.0-0.5 |
| hydroxyethyl-cellulose | 10-20 | 1-2 |
| colloidal silicon dioxide | 1-5 | 0.1-0.5 |

Formulation G: Peanut Low

| Components | Amount | % (W/W) |
|---|---|---|
| Light roasted peanut flour | 1-10 | 0.1-1 |
| Powdered sugar | 500-600 | 50-60 |
| Povidone K29-32 | 20-30 | 2-3 |
| Avicel PH101 | 400-450 | 40-45 |
| Colorant 1 | 10-20 | 1-2 |
| Flavor 1 | 1-5 | 0.1-0.5 |
| Flavor 2 | 0-5 | 0.0-0.5 |
| hydroxyethyl-cellulose | 10-20 | 1-2 |
| colloidal silicon dioxide | 1-5 | 0.1-0.5 |

Formulation F: Peanut High

| Components | Amount | % (W/W) |
|---|---|---|
| Light roasted peanut flour | 500-700 | 50-70 |
| Powdered sugar | 350-500 | 35-50 |
| Povidone K29-32 | 0-10 | 0-1 |
| Avicel PH101 | 0-50 | 0-5 |
| Colorant 1 | 1-20 | 0.1-2 |
| Colorant 2 | 0-20 | 0.0-2 |
| Opacifier | 5-20 | 0.5-20 |
| Flavor 1 | 1-5 | 0.1-0.5 |
| Flavor 2 | 0-5 | 0.0-0.5 |
| hydroxyethyl-cellulose | 10-20 | 1-2 |
| colloidal silicon dioxide | 1-5 | 0.1-0.5 |

Colorant 1 in these formulations is preferably selected from caramel colorant, red colorant Enocianin, Indigo yellow, Quinoline yellow, Quinizarine Green. Other colors like green, violet, pink, brown are possible too. Pharmaceutical grade (US Pharmacopoeia (USP) and European Pharmacopoeia (EP)) colorants can be obtained from various companies (Nigay, France; Emerald, Calif., USA; Narmada, India; Neelikon, France).

Colorant 2 in these formulations is preferably but not necessarily liquid and is different from or identical to colorant 1 and is preferably selected from caramel colorant, red colorant Enocianin, Indigo yellow, Quinoline yellow, Quinizarine Green. Other colors like green, violet, pink, brown are possible too. Pharmaceutical grade (US Pharmacopoeia (USP) and European Pharmacopoeia (EP)) colorants can be obtained from various companies (Nigay, France; Emerald, Calif., USA; Narmada, India; Neelikon, France).

The opacifier is any suitable opacifier, preferably Titanium dioxide (Carlo Erba, France), iron oxide (red, yellow, or black), erythrosine, or riboflavin (Proquimac, Spain). Such products are available in pharmaceutical grade (US Pharmacopoeia (USP) and European Pharmacopoeia (EP)).

Flavor 1 in these formulations is preferably selected from Orange flavor (Firmenich, Switzerland); Citric acid (Sigma-Fluka, Switzerland); sugar; Banana, Lemon, Caramel, Honey, Strawberry, Chocolate or Bubble gum. Such products are available in pharmaceutical grade (US Pharmacopoeia (USP) and European Pharmacopoeia (EP)).

Flavor 2 in these formulations is preferably but not necessarily liquid and is different from or identical to flavor 1 and is preferably selected from Orange flavor (Firmenich, Switzerland); Citric acid (Sigma-Fluka, Switzerland); sugar; Banana, Lemon, Caramel, Honey, Strawberry, Chocolate or Bubble gum. Such products are available in pharmaceutical grade (US Pharmacopoeia (USP) and European Pharmacopoeia (EP)).

Method to prepare Formulations F, G, and H: Colorant 1 is dissolved in water and Povidone is added. Alcohol may be used to facilitate the dissolution. Sucrose, Avicell and where indicated peanut flour, colorant 2 and opacifier are mixed. To facilitate the mixing, sugar may be added in portions before and after adding other dry components to the mix, rather than starting mixing with the entire amount of sugar. This mix is wetted using the solution of Povidone and colorant 1, and granules are formed using a high-speed mixer, during 5 minutes at 900 rpm. The resulting granules are forced through a stainless steel screen of 1.6 mm mesh size and dried in a fluidized bed dryer (Retsch) during 60 minutes at 45° C. Once dried, the granules are forced through a stainless steel screen of 0.8 mm mesh size. Dried granules are subsequently mixed with flavors and hydroxyethyl-cellulose and colloidal silicon dioxide.

Example 6. The Formulations Dissolve in Gastric Conditions

Dissolution tests were performed in standard dissolution apparatus described in current US and European Pharmacopoeias (apparatus 2, rotated at 100 rpm) in different dissolution media heated at 37° C. The formulation (the equivalent of 1 gram flour) is dissolved in a pH-neutral solution (incubation A, 750 ml) and in an acidic solution (incubation B, pH 1.2, 2, 3 or 4, 750 ml) and kept in suspension by gentle stirring. Samples are collected in time (at 0, 15, 30, 60, 90, and 120 minutes) and centrifuged to separate undissolved material (pellet) from dissolved material (supernatant).

Protein content is determined by taking the supernatant of the centrifuged sample, and measure the absorbance at 280 nm, using the dissolution fluid itself as a blank. Alternatively, measurement is performed using the Bradford method to determine protein concentration (Bradford et al., 1976). In short, the procedure is as follows: Solutions with known concentrations of bovine serum albumin (commercially available through Bio-Rad) were prepared to construct a calibration curve. Bradford reagent (protein assay dye reagent from Bio-Rad, 2.5 ml) was mixed with sample or solution for the calibration curve (0.05 ml). Mix was shaken, incubated for 30 minutes at room temperature, and the absorbance was read at 595 nm in 1 cm path length spectrophotometer. For samples with suspected low protein concentration, the micro-Bradford assay was used (commercially available through ThermoScientific). This reagent (0.4 ml) was mixed with sample (0.4 ml of a 20-fold diluted supernatant) or solution for the calibration curve (0.4 ml). Mix was shaken, incubated for 10 minutes at room temperature, and the absorbance was read at 595 nm in 1 cm path length spectrophotometer. Sample concentrations were calculated using the calibration curve.

The dissolution profile of formulations A and B under acidic conditions is described in FIG. 7. As shown, these two formulations dissolve very quickly, even quicker than the food allergen alone.

The dissolution profile of formulations D and E under acidic and neutral conditions is described in FIG. 8. As shown, these two formulations dissolve very quickly, substantially faster than peanut flour alone.

Dissolution profile of formulations F and H is represented in FIG. 9. As shown, formulation F dissolves quickly in the mouth, even more quickly than unformulated peanut flour. This formulation is thus very effective and useful for OIT.

Example 7: Release of Proteins, Major Allergens, and Allergenic Activity by Formulation a and Formulation B Under Gastric and Neutral Conditions Methods 7.1. Dissolution Experiments Dissolution experiments were performed at neutral pH to mimic mouth and oesophagus conditions, and at low pH to mimic stomach conditions. For neutral pH, a saliva-mimicking solution was prepared based on a recipe by Crea et al. (2015), containing 8.9 mM NaCl, 7.8 mM KCl, 11.5 mM $NaHCO_3$, 8.5 mM $K_2HPO_4$ and 3.5 mM $NH_4Cl$ (pH=7.6). Gastric acid was mimicked by a 0.1 M HCl solution (pH 1.0). 0.15 gram of reference peanut flour or 0.5 gram of test formula were weighed and transferred into capped 15 ml plastic round-bottom polystyrene tubes. 5 ml of pre-warmed (37° C.) test solvent was added to each tube and after vortexing for exactly 5 seconds the tubes were placed in an shaker incubator (New Brunswick) set at 300 rpm and an air temperature of 37° C. At the indicated time-points, tubes were vortexed for 2 seconds and a 0.5 ml sample was taken from halfway the suspension volume and transferred into an Eppendorf vial. The remaining volumes were further incubated for later time points. Each Eppendorf vial was immediately centrifuged (15000 rpm, 30 sec, rT) and supernatants were filtrated through a hydrophilic PVDF 0.45 μm Millex-HV low-protein binding filter (Millipore) into a new Eppendorf vial. These samples were stored at −20° C. The total time from removing an aliquot until having it passed through the filter was approximately 1 minute. Photographs were taken at indicated time points using a standard digital camera (no flash light).

7.2. Total Protein Concentration Determination

Protein concentration was determined by BCA protein assay, utilizing ready-to-use reagents from Sigma-Aldrich (BCA1 kit), and following the instructions of the manufacturer. Known quantities of bovine serum albumin, diluted in MilliQ water, were used to construct standard curves for quantification purposes. Where indicated, protein concentration was assessed by direct absorbance measurement of a 2 μl sample at 280 nm in a Nanodrop Lite spectrophotometer (Thermo Scientific), applying the extinction coefficients know for the main peanut allergens (UniProt database, ProtParam tool).

7.3. Quantitative SDS-PAGE

Samples were 6-fold diluted in MilliQ water and 4× Laemmli sample buffer (Bio-Rad), supplemented with β-mercaptoethanol (9:1, v/v). After heating for 10 minutes at 95° C., all samples were centrifuged (10 sec, 5000 rpm) and 13.6 μl of each supernatant was loaded onto Mini-PROTEAN TGX precast polyacrylamide gels (Bio-Rad), which were developed during 75 min under 100 volts at RT. Known quantities of Ara h1, h2, h3 and h6 standards and Precision Plus Dual Xtra molecular weight markers (Bio-Rad) were also loaded onto each gel. Protein bands were then stained by a Coomassie brilliant blue solution of 1 gr/L in methanol/acetic acid/MilliQ water (200:50:250, v/v) during 60 min at RT. Destaining of the gels was subsequently performed by a 3 hour incubation at RT in methanol/acetic acid/MilliQ water (300:5:250, v/v), while frequently refreshing the solvent. After a final wash of the gels in MilliQ water the gels were photographed GelDoc XR+ digital imaging station (Bio-Rad) in epi-white light with an exposure time of 60 milliseconds. Processing of the images was performed by GelAnalyzer 2010 software (http://www.gelanalyzer.com). This program determines band volumes (number of pixels within indicated borders multiplied by the intensity of each pixel within these borders) in each lane, after correction for background signal. Separate calibration curves were constructed for Ara h1, h2, h3 and h6, with quantities that fell within the linear range of detection (up to 4 μg per band, saturation occurred above this quantity). The concentrations of major allergens Ara h1, Ara h2, Ara h3, and Ara h6 are summed.

7.4. IgE-Binding by ELISA

A serum pool was composed of sera from 11 patients with peanut allergy. In this pool, specific IgE to total peanut (F13), Ara h 1, Ara h 2, Ara h 3, Ara h8, and Ara h9 was deomonstrated by ImmunoCap (ThermoFisher, USA). IgE-ELISA was performed essentially as described earlier (Koppelman, 2016) with some modifications. Maxisorp microtiter plates (Nunc Maxisorp F96 Thermo Scientific) were coated with 100 μL per well of 2.5 μg/ml of reference peanut flour in coating buffer (15 mM $Na_2CO_3$, 35 mM $NaHCO_3$, pH 9.6). After removal of the coating solution, 300 μl of blocking buffer (1% BSA in 20 mM Tris containing 0.9% NaCl, pH 7.4) was added to each well and plates were incubated for 1h at RT under agitation (650 rpm). Plates were washed 4× using wash buffer (20 mM Tris containing 0.9% w/v NaCl, pH 7.4 and 0.1% w/v Tween 20). Pooled human sera were diluted 50-fold in sample buffer (1% BSA in 20 mM Tris containing 0.9% w/v NaCl, pH 7.4, and 0.1% w/v Tween 20). Standards or test samples were also diluted in sample buffer and mixed 1:1 with the diluted pool serum. After a pre-incubation of at least 20 min at RT, 100 μl of each mixture was transferred to the plate, which was incubated for 2.5 hours (RT, 650 rpm agitation). Plates were washed 4× using wash buffer. HRP-conjugated mouse anti-human IgE Fc (Southern Biotech, USA) was diluted 5000-fold in sample buffer and 100 μl was added to each well. Plates were incubated for another 2.5 hours (RT, 650 rpm agitation) before washing 4× with wash buffer. 100 μl TMB substrate solution (Sigma-Aldrich) was added to each well for 30 min at RT to stain bound conjugate. HRP activity was terminated by 50 µl 1 M $H_2SO_4$ and absorbances were read at 450 nm in a CLARIOstar plate reader. Results are expressed as concentration (mg/ml) of reference peanut flour extract.

Results 7.5. Disintegration of Granules and Release of Protein

The disintegration of the non-coated and coated peanut-containing granules was evaluated in two media; one to mimic the conditions of the mouth and esophagus (saliva-like buffer, pH 7.6) and one to mimic the stomach conditions (HCl, pH 1.0), both at 37° C. and shaking conditions to avoid settling of the granules. FIG. 10 shows that at one hour, the non-coated formula A disintegrates completely at both pHs resulting in a milky solution visually comparable to that of the dissolution of reference peanut flour. The coated formulation B dissolves completely at pH 1.0 but, at pH 7.6, even after one hour of shaking at 37° C., the granules are essentially intact. The medium has a very light milky appearance, but it is clear that the coated granules resist dissolution at neutral pH.

In order to follow the kinetics of disintegration, samples were taken in time and analyzed for protein content. FIG. 11 shows that reference peanut flour dissolves at both pH conditions, but that dissolution reaches a higher plateau at low pH. This plateau is reached quickly (several minutes), probably due to the shaking conditions. The theoretical concentration, i.e., the maximum concentration that can be reached, is 25 mg/ml based on the amount of flour (0.5 gram), its protein content (50%) and medium volume (10 ml) in the dissolution experiment. The plateau value for reference flour is higher at low pH than at neutral pH, but still substantially lower than the theoretical value. The non-coated formulation A releases protein at both pH conditions. For both pH conditions, the plateau reached by non-coated formulation A is higher than what is achieved by reference flour alone. Accordingly, the formulation helps to dissolve the protein, which is a further advantage and surprising result of the invention. The coated formulation B shows a different behavior in terms of release of protein at neutral and low pH. At low pH, the coated formulation is similar to the non-coated formulation. In contrast, at neutral pH, hardly any protein is released in the tested time course. After 15 min, traces of protein are detectable but at approximately 30-fold lower concentration than for the non-coated formulation. At 30 min, more protein is released however still at about a 7-lower concentration than for the non-coated formulation. These results thus confirm the coating strongly reduces the release of protein at neutral pH, while the kinetics of release of protein at low pH are the same as is observed for the non-coated material. This demonstrates that the coating dissolves very quickly at low pH, and does not delay the release of protein in the stomach.

7.6. Release of Major Allergens

Next to analyzing total protein, we investigated the release of specific allergens from the non-coated and coated granules at different pHs by SDS-PAGE. This method resolves the four main allergens, Arah 1, h2, h3 and h6. Known amounts of these purified allergens were used to construct standard curves for quantitation. FIG. 12 shows the quantitative analysis of this SDS-PAGE. The intensity of the total Ara allergen bands as assessed by densitometry is represented. At neutral pH, both peanut flour and Formulation A release Ara allergens and Formulation A reaches a higher intensity than peanut flour itself. Formulation B at neutral pH does not release allergens up to 15 minutes of dissolution time. Formulation B at low pH shows release of allergens.

7.7. Release of Allergenic Activity

Further to testing the release of allergens, the release of allergenic activity was assessed for Formulations A and B at either neutral pH or low pH. FIG. 13 shows the release of allergenic activity, expressed as equivalent of a reference peanut extract. Non-coated Formulation A releases allergenic activity well, in both pH conditions, and to a greater extent than non-formulated peanut flour. The coated formulation B releases allergenic activity at low pH equally well as non-coated Formulation A, demonstrating that the coating does not hinder the release of allergenic activity at low pH. At neutral pH, in contrast, the coated Formulation B does not release allergenic activity up to 4 minutes and at later time points only releases a minor amount compared to the low pH condition and non-coated Formulation A at neutral pH.

7.8. Discussion and Conclusions

Non-coated Formulation A disintegrates, releases protein, releases major allergens, and releases allergenic activity to a greater extent than peanut flour itself, at both low pH and neutral pH. This demonstrates an unexpected advantageous effect of the formulation. Without being bound by theory, this unexpected effect may be explained by the granulation process: peanut flour is dispersed in liquid in the presence of excipients, at elevated temperature. This step may increase the water-accessibility of the protein by interacting with the residual fat present in the flour (12%). Coated Formulation B disintegrates, releases protein, releases major allergens, and releases allergenic activity to a greater extent than peanut flour itself, only at low pH. This demonstrates that the coating does not prevent dissolution at low pH. At neutral pH, coated Formulation B shows a strongly reduced rate of disintegration, release of protein, release of major allergens, and release of allergenic activity, compared to Formulation A or reference peanut flour. Thus, Formulation B is suitable for preventing exposure of the mouth and esophagus to allergens.

Example 8: Production of Coated and Non-Coated Formulations

The following specific formulations are produced. Production was performed essentially as disclosed in examples 2 and 3. More specifically, Povidone is dissolved in a suitable volume of water and peanut flour is then suspended. The resulting suspension is sprayed onto the sucrose cores in a suitable fluidized bed device (Glatt GPCG-1) equipped with a bottom spray insert, with the following process parameters:

Inlet temperature: 58-60° C.
Product temperature: 37° C.
Air volume: 70-80 m³/h
Spraying pressure: 2.5-2.8 bar.

For Formulation A5, the same manufacturing conditions as for Formulation A2 were applied, except that PVA was suspended in a suitable amount of water, then heated until boiling point and allowed to return to room temperature with stirring until complete dissolution.

For Formulation B1, talc is dispersed in a suitable volume of acetone-isopropanol mixture and the suspension is homogenized (for example with Ultra-Turrax homogenizer). Macrogol is dissolved in a suitable volume of water and the resulting solution is mixed with the Eudragit solution during 15 min. The talc suspension is added under stirring and the resulting suspension is filtrated through a suitable stainless steel mesh screen and then sprayed onto the spheres obtained at stage A in a suitable fluidized bed device (Glatt GPCG-1) equipped with a bottom spray insert, with the following process parameters:
Inlet temperature: 36-38° C.
Product temperature: 30-31° C.
Air volume: 74-90 m3/h
Spraying pressure: 2.5-2.8 bar.

Formulations B1, B2, B4, and B5 can optionally be treated with 0.5 to 2% of Aerosil 200 to avoid further agglomeration during storage. This treatment can be done by applying Aerosil 200 during the coating step with Eudragit, Macrogol, and talc, or as a subsequent step. Similarly, Formulation B3-1 can optionally be treated with 0.5 to 2% of Syloid 72FO to avoid further agglomeration during storage. Regarding Formulation B3-2, sodium lauryl sulfate was dispersed in water and stearic acid was added. After 15 minutes, Eudragit E PO was added. Talc was added after 90 minutes and dispersed by mixing with an Ultra-Turrax. This mixture was coated onto Formulation A3 using top-spray method (Würster):
Inlet temperature: 44° C.
Product temperature: 30-31° C.
Air volume: 80 m3/h
Spraying pressure: 2.4 bar.

Formulation B3-2 can also optionally be treated with 0.5 to 2% of Aerosil 200 to avoid further agglomeration during storage.

For Formulation B6, Kollicoat Smartseal coating was used as an alternative to Eudragit 12.5%. Briefly, dibutyl sebacate was dispersed in water and talc was added. Kollicoat Smartseal was added under shaking conditions (45 minutes). This mixture was coated onto Formulation A3 using top-spray method (Würster):
Inlet temperature: 45° C.
Product temperature: 40° C.
Air volume: 90 m3/h
Spraying pressure: 2.5 bar.

Formulation B6 can optionally be treated with 0.5 to 2% of Aerosil 200 to avoid further agglomeration during storage.

Formulation A1

| Components | Amount (g) |
| --- | --- |
| Light roasted peanut flour | 295 |
| Povidone K30 (binder) | 147 |
| Core (sucrose) particles (400-600 μm) | 420 |

Formulation A2

| Components | Amount (g) |
| --- | --- |
| Light roasted peanut flour | 294 |
| Povidone K30 (binder) | 147 |
| Core (sucrose) particles (180-250 μm) | 420 |

Formulation A3

| Components | Amount (g) |
| --- | --- |
| Light roasted peanut flour | 294 |
| Povidone K30 (binder) | 147 |
| Core (lactose) particles (250 μm) | 420 |

Formulation A4

| Components | Amount (g) |
| --- | --- |
| Light roasted peanut flour | 294 |
| Pharmacoat 603 (binder) | 88.2 |
| Core (sucrose) particles (250-355 μm) | 420 |

Formulation A5

| Components | Amount (g) |
| --- | --- |
| Light roasted peanut flour | 210 |
| PVA 10-98 (binder) | 10.5 |
| Core (sucrose) particles (250-355 μm) | 300 |

Formulation B1

| Components | Amount (g) |
| --- | --- |
| Formulation A1 | 600 |
| Eudragit E 12.5% (coat) | 414 |
| Macrogol (coat excipient, platicizer) | 5.175 |
| Talc (micronized) (coat excipient, anti-adherent to avoid sticking of granules) | 25.875 |

Formulations B2, B4, and B5 are based on Formulations A2, A4, and A5, respectively.

Formulation B3-1

| Components | Amount (g) |
| --- | --- |
| Formulation A3 | 540 |
| Eudragit E 12.5% (coat) | 372 |
| Macrogol (coat excipient, platicizer) | 4.658 |
| Talc (micronized) (coat excipient, anti-adherent to avoid sticking of granules) | 23.288 |

Formulation B3-2

| Components | Amount (g) |
| --- | --- |
| Formulation A3 | 540 |
| Eudragit E PO (coat) | 89.1 |
| Sodium lauryl sulfate | 5.94 |
| Stearic acid | 14.85 |
| Talc (micronized) (coat excipient, anti-adherent to avoid sticking of granules) | 44.5 |

Formulation B6

| Components | Amount (g) |
|---|---|
| Formulation A | 600 |
| Kollicoat Smartseal 30D (coat) | 268.1 |
| Talc (micronized) (coat excipient, anti-adherent to avoid sticking of granules) | 42.55 |
| Dibutyl sebacate | 8.05 |

For the Formulations described in this Example, placebo Formulations were manufactured as well, by using the same manufacturing procedures applied for the corresponding Formulations, except that peanut flour was omitted.

Example 9: Dissolution of Formulations A, A3, B, B6, and B3-2, and their Placebo Formulations, at Neutral pH and Gastric Conditions Dissolution tests were performed in standard dissolution apparatus described in current US and European Pharmacopoeias (apparatus 2, rotated at 100 rpm) in different dissolution media heated at 37° C. The formulation (the equivalent of 1 gram flour) is dissolved in a pH-neutral solution (8.9 mM NaCl, 7.8 mM KCl, 11.5 mM NaHCO$_3$, 8.5 mM K$_2$HPO$_4$ and 3.5 mM NH$_4$Cl in MilliQ water and with pH adjusted with HCl to 7.6, 500 ml) and in an acidic solution (0.1 N HCl, pH=1, 500 ml), at stirring conditions (100 rpm). Samples are collected in time (at 1, 2, 4, 8, 15, 30, 45, and 60 minutes) and filtered to separate undissolved material (pellet) from dissolved material (supernatant). Pictures were taken at indicated time points by taking a sample at 60 minutes with a large spoon and pouring this sample in a 10 ml glass test tube.

FIG. 14, panel A, shows that reference peanut flour disintegrates equally well at neutral (7.6) pH and acidic (1.0) pH. Panel B shows that non-coated formulation A disintegrates at both pH conditions too, while Formulations B and B6 disintegrate at low pH (gastric conditions), but not at neutral pH (mouth conditions). Panel C shows that non-coated Formulation A3 dissolved equally well at neutral and low pH, while coated Formulation B3-2 disintegrates at low pH, but remains as granules (dispersed in the fluid) at neutral pH. This shows that the coating, Eudragit E PO, prevents disintegration at neutral pH in a similar way as Eudragit E 12.5% (organic solution). An advantage of Eudragit E PO over Eudragit E 12.5% is that it can be applied without the use of organic solvents.

Dissolution was quantified by means of a spectroscopic method (Pierce BCA Protein Assay Kit (ThermoFisher Scientific)). This method reacts with protein and several excipients and can be used to study overall dissolution of granules. Due to potentially different reactivity of excipients, the results of different formulations cannot be compared. When a single formula is considered, the results of different dissolution conditions can be compared, because the same components and excipients are present. Results are shown in arbitrary units. FIG. 15 shows that the Formulations B, B6 and B3-2, which are coated with Eudragit12.5%, Kollicoat Smartseal, and Eudragit E PO, respectively, dissolve rapidly at low pH (pH=1), while they remain essentially intact at neutral pH. At neutral pH, Formulations B and B6 remain stable for at least 8 minutes, and show only very minor dissolution up to 45-60 minutes. These results illustrate the unexpected properties of Eudragit 12.5% and Kollicoat Smartseal at neutral pH, which are very stable, while quickly dissolve under acidic conditions.

REFERENCES

Bradford M M. A rapid and sensitive method for the quantitation of microgram quantities of protein utilizing the principle of protein-dye binding. Anal Biochem. 1976 May 7; 72:248-54.
Cochrane S A, Salt L J, Wantling E, Rogers A, Coutts J, Ballmer-Weber B K, Fritsche P, Fernandez-Rivas M, Reig I, Knulst A, Le T M, Asero R, Beyer K, Golding M, Crevel R, Clare Mills E N, Mackie A R. Development of a standardized low-dose double-blind placebo-controlled challenge vehicle for the EuroPrevall project. Allergy. 2012; 67(1):107-13.
May C D. Objective clinical and laboratory studies of immediate hypersensitivity reactions to foods in asthmatic children. J Allergy Clin Immunol 1976; 58:500-15.
Nowak-Wegrzyn A, Assa'ad A H, Bahna S L, Bock S A, Sicherer S H, Teuber S S; Work Group report: oral food challenge testing. J Allergy Clin Immunol. 2009 June; 123(6 Suppl):S365-83.
Nowak-Wegrzyn A, Sampson H A. Future therapies for food allergies. J Allergy Clin Immunol. 2011 March; 127(3): 558-73.
Ridolo E, De Angelis G L, Dall'aglio P. Eosinophilic esophagitis after specific oral tolerance induction for egg protein. Ann Allergy Asthma Immunol 2011; 106:73-4.
Rolinck-Werninghaus C, Staden U, Mehl A, Hamelmann E, Beyer K, Niggemann B. Specific oral tolerance induction with food in children: transient or persistent effect on food allergy? Allergy. 2005 October; 60(10):1320-2.
Sampson H A, Gerth van Wijk R, Bindslev-Jensen C, Sicherer S, Teuber S S, Burks A W, Dubois A E, Beyer K, Eigenmann P A, Spergel J M, Werfel T, Chinchilli V M. Standardizing double-blind, placebo-controlled oral food challenges: American Academy of Allergy, Asthma & Immunology-European Academy of Allergy and Clinical Immunology PRACTALL consensus report. J Allergy Clin Immunol. 2012 December; 130(6):1260-74.
Sanchez-Garcia S, Rodriguez dR, Escudero C, Martinez-Gomez M J, Ibanez M D. Possible eosinophilic esophagitis induced by milk oral immuno-therapy. J Allergy Clin Immunol. 2012; 129:1155-7.
Spergel J M, Andrews T, Brown-Whitehorn T F, Beausoleil J L, Liacouras C A. Treatment of eosinophilic esophagitis with specific food elimination diet directed by a combination of skin prick and patch tests. Ann Allergy Asthma Immunol. 2005 October; 95(4):336-43.
Thoke, S B, 2012. A Seminar on Microencapsulation techniques and application. Dept of Pharmaceutics, University of Babhulgaon/Yeola, India.
Wasserman R L, Sugerman R W, Mireku-Akomeah A R, Gallucci A, Pence D, Long N A. Peanut oral immunotherapy (OIT) of food allergy (F A) carries a significant risk of eosinophilic esophagitis (EoE) [abstract]. J Allergy Clin Immunol 2011; 127: Abstract 28.

The invention claimed is:
1. A pharmaceutical product suitable for oral administration of a peanut allergen, the pharmaceutical product comprising particles, said particles having a size or average size between 1 μm and 10 mm,
said particles comprising a neutral core surrounded by a first layer comprising heat treated peanut allergen, wherein said neutral core has a diameter of about 90-1000 μm and comprises a polyhydroxylated compound or a sugar, and said particles further comprise a stomach-labile coating layer stable at neutral pH, said coating layer surrounding said first layer and said coating layer comprising cationic copolymers based on dimethylaminoethyl methacrylate, butyl methacrylate, methyl methacrylate or mixtures thereof, and wherein the product releases essentially all the heat treated peanut allergen in the stomach.

2. The product of claim 1, wherein said particles have a size or average size between 10 μm and 1.5 mm or between 50 μm and 1000 μm.

3. The product of claim 1, wherein said particles are essentially spherical.

4. The product of claim 1, wherein the particles do not dissolve in the oral cavity.

5. The product of claim 1, wherein the first layer comprises from 70 to 100% by weight of the total amount of peanut allergen of the product, said layer being homogeneous and covering the entire surface of the core.

6. The product of claim 1, wherein the peanut allergen is a peanut extract or an isolated or purified peanut allergen or a mixture thereof.

7. The product of claim 1, wherein the peanut allergen is a low fat peanut allergen preparation having a fat content of less than 20%.

8. The product of claim 1, wherein the peanut allergen is a peanut flour preparation.

9. A pharmaceutical composition comprising a product of claim 1.

10. A method of delivering a peanut allergen to the stomach of a subject comprising the oral administration of a product according to claim 1 to said subject.

11. A method of determining reactivity of a subject to a peanut allergen comprising administering a product according to claim 1 to a subject and determining the reactivity of the subject to said peanut allergen.

12. A method of inducing tolerance to a peanut allergen in a subject allergic to said peanut allergen comprising administering a product according to claim 1 containing said peanut allergen to said subject.

13. The product of claim 1, wherein the heat treated peanut allergen comprises one or several peanut proteins selected from Ara h1, Ara h2, Ara h3, Ara h4, Ara h5, Ara h6, Ara h7, Ara h8, Ara h9, Ara h10, Ara h11, Ara h12, Ara h13, Ara h14, Ara h15, Ara h16, or Ara h17, or fragments thereof.

14. The product of claim 1, wherein the neutral core comprises a compound selected from the group consisting of lactose, sucrose, mannitol and cellulose.

15. The product of claim 1, wherein the neutral core is selected from a microcrystalline cellulose sphere and a sugar sphere.

16. The product of claim 1, wherein the first layer comprises the peanut allergen and an excipient.

17. The product of claim 1, wherein the first layer comprises the peanut allergen and one or several pharmaceutically-compatible (co-)polymers selected from the group consisting of sugars, (co-)polymers based on cellulose, (meth)acrylate, alginate, maltodextrins, cylodextrine, gelatin, povidone, poly-ethylene glycol (PEG), xanthan gum, ethylcellulose, methylcellulose, carboxymethylcellulose (CMC) and hydroxypropylcellulose (HPMC).

18. The product of claim 1, wherein the peanut allergen is a low fat peanut allergen preparation having a fat content of about 20%.

* * * * *

UNITED STATES PATENT AND TRADEMARK OFFICE
CERTIFICATE OF CORRECTION

PATENT NO. : 10,300,133 B2  
APPLICATION NO. : 15/423820  
DATED : May 28, 2019  
INVENTOR(S) : Pierre-Henri Benhamou et al.

Page 1 of 1

It is certified that error appears in the above-identified patent and that said Letters Patent is hereby corrected as shown below:

In the Specification

<u>Column 23,</u>
Line 33, "Formulation a" should read --Formulation A--.

Signed and Sealed this
Twenty-sixth Day of November, 2019

Andrei Iancu
*Director of the United States Patent and Trademark Office*